United States Patent
Verhaegh et al.

(10) Patent No.: US 11,309,059 B2
(45) Date of Patent: Apr. 19, 2022

(54) MEDICAL PROGNOSIS AND PREDICTION OF TREATMENT RESPONSE USING MULTIPLE CELLULAR SIGNALLING PATHWAY ACTIVITIES

(71) Applicant: KONINKLIJKE PHILIPS N.V., Eindhoven (NL)

(72) Inventors: Wilhelmus Franciscus Johannes Verhaegh, Eindhoven (NL); Hendrik Jan Van Ooijen, Eindhoven (NL); Anja Van De Stolpe, Eindhoven (NL); Marcia Alves De Inda, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1179 days.

(21) Appl. No.: 14/785,400

(22) PCT Filed: Apr. 24, 2014

(86) PCT No.: PCT/EP2014/058326
§ 371 (c)(1),
(2) Date: Oct. 19, 2015

(87) PCT Pub. No.: WO2014/174003
PCT Pub. Date: Oct. 30, 2014

(65) Prior Publication Data
US 2016/0110494 A1  Apr. 21, 2016

(30) Foreign Application Priority Data

Apr. 26, 2013  (EP) .................................... 13165471

(51) Int. Cl.
| | | |
|---|---|---|
| G16B 5/00 | (2019.01) | |
| G16B 20/00 | (2019.01) | |
| C12Q 1/6886 | (2018.01) | |
| G16H 50/30 | (2018.01) | |
| G16B 25/10 | (2019.01) | |
| G16B 25/00 | (2019.01) | |
| G16B 5/20 | (2019.01) | |

(52) U.S. Cl.
CPC ............. *G16B 5/20* (2019.02); *C12Q 1/6886* (2013.01); *G16B 5/00* (2019.02); *G16B 20/00* (2019.02); *G16B 25/10* (2019.02); *G16H 50/30* (2018.01); *C12Q 2600/118* (2013.01); *C12Q 2600/158* (2013.01); *G16B 25/00* (2019.02)

(58) Field of Classification Search
None
See application file for complete search history.

(56) References Cited

U.S. PATENT DOCUMENTS

2011/0003707 A1  1/2011  Goix
2016/0110494 A1  4/2016  Verhaegh

FOREIGN PATENT DOCUMENTS

| EP | 2549399 A1 | 1/2013 |
|---|---|---|
| RU | 2376272 C2 | 12/2009 |
| WO | 2006124836 A1 | 11/2006 |
| WO | 2012104764 A2 | 8/2012 |
| WO | 2013011479 A2 | 1/2013 |
| WO | 2013084144 A1 | 6/2013 |
| WO | 2014102668 A1 | 7/2014 |

OTHER PUBLICATIONS

Lee, Eunjung et al "Inferring Pathway Activity toward Precise Disease Classification", PLoS Computational Biology, vol. 4, No. 11, 2008.
Ochs, Michael F. et al "Detection of Treatment-Induced Changes in Signaling Pathways in Gastrointestinal Stromal Tumors using Transcriptomic Data", Cancer Research, 2009.
Paik, Soonmyung et al "A Multigene Assay to Predict Recurrence of Tamoxifen-Treated, Node-Negative Breast Cancer" The New England Journal of Medicine, 2004.
Su, Junjie et al "Accurate and Reliable Cancer Classification based on Probabilistic Inference of Pathway Activity", PLoS One, vol. 4, Issue 12, Dec. 2009.
Wei, Zhi et al Nonparametric Pathway-Based Regression Models for Analysis of Genomic Data, Biostatistics, vol. 8, No. 2, 2007.
Soderberg, Ola et al "Direct Observation of Individual Endogenous Protein Complexes in situ by Proximity Ligation", Nature Methods, 2006.
Fan, Cheng et al "Concordance Among Gene-Expression-Based Predictors for Breast Cancer", The New England Journal of Medicine, 2006.
Hatzis, Pantelis et al "Genome-Wide Pattern of TCF7L2/TCF4 Chromatin Occupancy in Colorectal Cancer Cells", Molecular and Celluar Biology, 2008.
Nusse, R. "Wnt Target Genes", The Wnt HomePage, 2012, www.stanford.edu/group/nusselab/cgi-bin/wnt/target_genes.
De Sousa E Melo, F. et al "Methylation of Cancer-Stem-Cell-Associated Wnt Target Genes Predicts Poort Prognosis in Colorectal Cancer Patients", Cell Stem Cell, 2011.
Van De Wetering, Marc et al "The Beta-Catenin/TCF-4 Complex Imposes a Crypt Progenitor Phenotype n Colorectal Cancer Cells", Cell, vol. 111, 2002.
DeRoo, Bonnie J. et al "Estrogen Receptors and Human Disease", The Joournal of Clinical Investigation, Review Series, vol. 116, N. 3, Mar. 2006, pp. 561-570.

*Primary Examiner* — Olivia M. Wise

(57) ABSTRACT

A method for determining a risk score that indicates a risk that a clinical event will occur within a certain period of time. The risk score is based at least in part on a combination of inferred activities of two or more cellular signaling pathways in a tissue and/or cells and/or a body fluid of a subject. The cellular signaling pathways comprise a Wnt pathway, an ER pathway, an HH pathway, and/or an AR pathway. The risk score is defined such that the indicated risk that the clinical event will occur within the certain period of time decreases with an increasing PER and increases with an increasing max(PWnt, PHH), wherein PER, PWnt, and PHH denote the inferred activity of the ER pathway, the Wnt pathway, and the HH pathway, respectively.

16 Claims, 7 Drawing Sheets

MEDICAL PROGNOSIS AND PREDICTION OF TREATMENT RESPONSE USING MULTIPLE CELLULAR SIGNALLING PATHWAY ACTIVITIES

CROSS-REFERENCE TO PRIOR APPLICATIONS

This application is the U.S. National Phase application under 35 U.S.C. § 371 of International Application No. PCT/EP2014/058326, filed on Apr. 24, 2014, which claims the benefit of European Patent Application No. 13165471.7, filed on Apr. 26, 2013. These applications are hereby incorporated by reference herein.

FIELD

The subject matter described herein mainly relates to bioinformatics, genomic processing arts, proteomic processing arts, and related arts.

BACKGROUND

Genomic and proteomic analyses have substantial realized and potential promise for clinical application in medical fields such as oncology, where various cancers are known to be associated with specific combinations of genomic mutations/variations/abnormal methylation patterns and/or high or low expression levels for specific genes, which play a role in growth and evolution of cancer, e.g., cell proliferation and metastasis. For example, the Wnt signaling pathway affects regulation of cell proliferation, and is highly regulated. High Wnt pathway activity due to loss of regulation has been correlated to cancer, among which with malignant colon tumors. While not being limited to any particular theory of operation, it is believed that deregulation of the Wnt pathway in malignant colon cells leads to high Wnt pathway activity that in turn causes cell proliferation of the malignant colon cells, i.e., spread of colon cancer. On the other hand, abnormally low pathway activity might also be of interest, for example in the case of osteoporosis. Other pathways which play similar roles in cell division, function and/or differentiation in health and disease are cellular signaling pathways (e.g., ER, PR, AR, PPAR, GR, VitD, TGFbeta, Notch, Hedgehog, FGF, NFkappaB, VEGF, and PDGF).

Technologies for acquiring genomic and proteomic data have become readily available in clinical settings. For example, measurements by microarrays are routinely employed to assess gene expression levels, protein levels, methylation, and so forth. Automated gene sequencing enables cost-effective identification of genetic variations/mutations/abnormal methylation patterns in DNA and mRNA. Quantitative assessment of mRNA levels during gene sequencing holds promise as a clinical tool for assessing gene expression levels.

One of the main challenges for a therapist, e.g., an oncologist, is to make an educated guess on the prognosis of the patient, since this information influences treatment choices. Individual patients cancer tissue sample-based genomics, transcriptomics and proteomics (and other "omics") analysis provides information which can potentially contribute to the prognostic assessment of the patient. However interpretation of these complex data to extract the relevant clinical information has proven to be a challenge, yet largely unsolved. Prognosis of a patient can be indicated in a quantitative manner in several ways, as for example: "time to recurrence", or "time to metastasis", or "survival time", or "risk at death due to the disease or treatment".

SUMMARY

The present disclosure provides new and improved methods and apparatuses as disclosed herein.

In accordance with a main aspect of the present invention, the above problem is solved by a specific method for determining a risk score that indicates a risk that a clinical event will occur within a certain period of time, namely a method comprising:

inferring activity of two or more cellular signaling pathways in a tissue and/or cells and/or a body fluid of a subject based at least on the expression levels of one or more target gene(s) of the cellular signaling pathways measured in an extracted sample of the tissue and/or the cells and/or the body fluid of the subject, and determining a risk score that indicates a risk that a clinical event will occur within a certain period of time, wherein the risk score is based at least in part on a combination of the inferred activities, wherein the cellular signaling pathways comprise a Wnt pathway, an ER (Estrogen Receptor) pathway, an HH (Hedgehog) pathway, and/or an AR (Androgen Receptor) pathway, wherein the cellular signaling pathways comprise the ER pathway, the Wnt pathway, and the HH pathway, and wherein the risk score is defined such that the indicated risk that the clinical event will occur within the certain period of time decreases with an increasing $P_{ER}$ and increases with an increasing max($P_{Wnt}$, $P_{HH}$), wherein $P_{ER}$, $P_{Wnt}$, and $P_{HH}$ denote the inferred activity of the ER pathway, the Wnt pathway, and the HH pathway, respectively.

The subject may be a human or an animal, and, in particular, a medical subject. Moreover, the "target gene(s)" may be "direct target genes" and/or "indirect target genes" (as described herein).

The Wnt pathway, the ER pathway, the HH pathway, and the AR pathway are preferably defined as the cellular signaling pathway that ultimately leads to transcriptional activity of the transcription factor (TF) complexes associated with the pathway. Preferably, these consist of at least β-catenin/TCF4, ERα dimer, a GLI family member, and AR, respectively.

The inferring of the activity of the cellular signaling pathways in the tissue and/or the cells and/or the body fluid of the subject may be performed, for example, by inter alia (i) evaluating at least a portion of a probabilistic model, preferably a Bayesian network, representing the cellular signaling pathways for a set of inputs including at least the expression levels of the one or more target gene(s) of the cellular signaling pathways measured in the tissue and/or the cells and/or the body fluid (e.g., staining on a tissue slide or cells) or in an extracted sample of the tissue and/or the cells and/or the body fluid of the subject, (ii) estimating a level in the tissue of the subject of at least one transcription factor (TF) element, the at least one TF element controlling transcription of the one or more target gene(s) of the cellular signalling pathways, the estimating being based at least in part on conditional probabilities relating the at least one TF element and the expression levels of the one or more target gene(s) of the cellular signaling pathway measured in the extracted sample of the subject, and (iii) inferring the activity of the cellular signaling pathways based on the estimated level in the tissue sample and/or the cells sample and/or the body fluid sample of the transcription factor. This is described in detail in the published European patent application EP 2 549 399 A1 ("Assessment of Wnt pathway activity using probabilistic modeling of target gene expressions") and, in particular, in the published international patent application WO 2013/011479 A2 ("Assessment of cellular signaling pathway activity using probabilistic modeling of target gene expression"), the contents of which are herewith incorporated in their entirety.

In an exemplary alternative, the inferring of the activity of one or more of the cellular signaling pathways in the tissue and/or the cells and/or the body fluid of the subject may be performed by inter alia (i) determining a level of a transcription factor (TF) element in the extracted sample of the tissue and/or the cells and/or the body fluid of the subject, the TF element controlling transcription of the one or more target gene(s) of the cellular signaling pathway, the determining being based at least in part on evaluating a mathematical model relating expression levels of the one or more target gene(s) of the cellular signaling pathway to the level of the TF element, the model being based at least in part on one or more linear combination(s) of expression levels of the one or more target gene(s), and (ii) inferring the activity of the cellular signaling pathway in the tissue and/or the cells and/or the body fluid of the subject based on the determined level of the TF element in the extracted sample of the tissue and/or the cells and/or the body fluid of the subject. This is described in detail in the unpublished US provisional patent application U.S. 61/745,839 resp. the unpublished international patent application PCT/IB2013/061066 ("Assessment of cellular signaling pathway activity using linear combination(s) of target gene expressions").

Preferably, the cellular signaling pathways comprise at least one cellular signaling pathway that plays a role in cancer.

Particularly preferred is a method wherein the cellular signaling pathways comprise the Wnt pathway and/or the HH pathway, and wherein the risk score is defined such that the indicated risk that the clinical event will occur within the certain period of time monotonically increases with an increasing inferred activity of the Wnt pathway and/or an increasing inferred activity of the HH pathway.

Also particularly preferred is a method wherein the cellular signaling pathways comprise the ER pathway, and wherein the risk score is defined such that the indicated risk that the clinical event will take place within the certain period of time monotonically decreases with an increasing inferred activity of the ER pathway.

Further preferred is a method wherein the combination of the inferred activities comprises the expression $$-\alpha \cdot P_{ER} + \beta \cdot \max(P_{Wnt}, P_{HH}),$$

wherein $P_{ER}$, $P_{Wnt}$, and $P_{HH}$ denote the inferred activity of the ER pathway, the Wnt pathway, and the HH pathway, respectively, a and B are non-negative constant scaling factors, and the indicated risk that the clinical event will occur within the certain period of time monotonically increases with an increasing value of the expression.

Particularly preferred is a method wherein the inferring comprises:
inferring activity of a Wnt pathway in the tissue and/or the cells and/or the body fluid of the subject based at least on expression levels of one or more, preferably at least three, target gene(s) of the Wnt pathway measured in the extracted sample of the tissue and/or the cells and/or the body fluid of the subject selected from the group consisting of: KIAA1199, AXIN2, RNF43, TBX3, TDGF1, SOX9, ASCL2, IL8, SP5, ZNRF3, KLF6, CCND1, DEFA6 and FZD7,
and/or
inferring activity of an ER pathway in the tissue and/or the cells and/or the body fluid of the subject based at least on expression levels of one or more, preferably at least three, target gene(s) of the ER pathway measured in the extracted sample of the tissue and/or the cells and/or the body fluid of the subject selected from the group consisting of: GREB1, PGR, XBP1, CA12, SOD1, CTSD, IGFBP4, TFF1, SGK3, NRIP1, CELSR2, WISP2, and APIB1,
and/or
inferring activity of an HH pathway in the tissue and/or the cells and/or the body fluid of the subject based at least on expression levels of one or more, preferably at least three, target gene(s) of the HH pathway measured in the extracted sample of the tissue and/or the cells and/or the body fluid of the subject selected from the group consisting of: GLI1, PTCH1, PTCH2, IGFBP6, SPP1, CCND2, FST, FOXL1, CFLAR, TSC22D1, RAB34, S100A9, S100A7, MYCN, FOXM1, GL13, TCEA2, FYN, and CTSL1,
and/or
inferring activity of an AR pathway in the tissue and/or the cells and/or the body fluid of the subject based at least on expression levels of one or more, preferably at least three, target gene(s) of the AR pathway measured in the extracted sample of the tissue and/or the cells and/or the body fluid of the subject selected from the group consisting of: KLK2, PMEPA1, TMPRSS2, NKX3_1, ABCC4, KLK3, FKBP5, ELL2, UGT2B15, DHCR24, PPAP2A, NDRG1, LRIG1, CREB3L4, LCP1, GUCY1A3, AR, and EAF2.

Further preferred is a method wherein the inferring is further based on:
expression levels of at least one target gene of the Wnt pathway measured in the extracted sample of the tissue and/or the cells and/or the body fluid of the subject selected from the group consisting of: NKD1, OAT, FAT1, LEF1, GLUL, REG1B, TCF7L2, COL18A1, BMP7, SLC1A2, ADRA2C, PPARG, DKK1, HNF1A, and LECT2,
and/or
expression levels of at least one target gene of the ER pathway measured in the extracted sample of the tissue and/or the cells and/or the body fluid of the subject selected from the group consisting of: RARA, MYC, DSCAM, EBAG9, COX7A2L, ERBB2, PISD, KRT19, HSPB1, TRIM25, PTMA, COL18A1, CDH26, NDUFV3, PRDM15, ATP5J, and ESR1,
and/or
expression levels of at least one target gene of the HH pathway measured in the extracted sample of the tissue and/or the cells and/or the body fluid of the subject selected from the group consisting of: BCL2, FOXA2, FOXF1, H19, HHIP, IL1R2, JAG2, JUP, MIF, MYLK, NKX2.2, NKX2.8, PITRM1, and TOM1.
and/or
expression levels of at least one target gene of the AR pathway measured in the extracted sample of the tissue and/or the cells and/or the body fluid of the subject selected from the group consisting of: APP, NTS, PLAU, CDKN1A, DRG1, FGF8, IGF1, PRKACB, PTPN1, SGK1, and TACC2.

Another aspect of the present disclosure relates to a method (as described herein), further comprising:
assigning the subject to at least one of a plurality of risk groups associated with different indicated risks that the clinical event will occur within the certain period of time, and/or deciding a treatment recommended for the subject based at least in part on the indicated risk that the clinical event will occur within the certain period of time.

The present disclosure also relates to a method (as described herein), comprising:

inferring activity of a Wnt pathway in the tissue and/or the cells and/or the body fluid of the subject based at least on expression levels of two, three or more target genes of a set of target genes of the Wnt pathway measured in the extracted sample of the tissue and/or the cells and/or the body fluid of the subject, and/or inferring activity of an ER pathway in the tissue and/or the cells and/or the body fluid of the subject based at least on expression levels of two, three or more target genes of a set of target genes of the ER pathway measured in the extracted sample of the tissue and/or the cells and/or the body fluid of the subject, and/or inferring activity of an HH pathway in the tissue and/or the cells and/or the body fluid of the subject based at least on expression levels of two, three or more target genes of a set of target genes of the HH pathway measured in the extracted sample of the tissue and/or the cells and/or the body fluid of the subject, and/or inferring activity of an AR pathway in the tissue and/or the cells and/or the body fluid of the subject based at least on expression levels of two, three or more target genes of a set of target genes of the AR pathway measured in the extracted sample of the tissue and/or the cells and/or the body fluid of the subject.

Preferably, the set of target genes of the Wnt pathway includes at least nine, preferably all target genes selected from the group consisting of KIAA1199, AXIN2, RNF43, TBX3, TDGF1, SOX9, ASCL2, IL8, SP5, ZNRF3, KLF6, CCND1, DEFA6, and FZD7, and/or the set of target genes of the ER pathway includes at least nine, preferably all target genes selected from the group consisting of: GREB1, PGR, XBP1, CA12, SOD1, CTSD, IGFBP4, TFF1, SGK3, NRIP1, CELSR2, WISP2, and AP1B1, and/or the set of target genes of the HH pathway includes at least nine, preferably all target genes selected from the group consisting of: GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN, and CTSL1, and/or the set of target genes of the AR pathway includes at least nine, preferably all target genes selected from the group consisting of: KLK2, PMEPA1, TMPRSS2, NKX3_1, ABCC4, KLK3, FKBP5, ELL2, UGT2B15, DHCR24, PPAP2A, NDRG1, LRIG1, CREB3L4, LCP1, GUCY1A3, AR, and EAF2.

Particularly preferred is a method wherein the set of target genes of the Wnt pathway further includes at least one target gene selected from the group consisting of: NKD1, OAT, FAT1, LEF1, GLUL, REG1B, TCF7L2, COL18A1, BMP7, SLC1A2, ADRA2C, PPARG, DKK1, HNF1A, and LECT2, and/or the set of target genes of the ER pathway further includes at least one target gene selected from the group consisting of: RARA, MYC, DSCAM, EBAG9, COX7A2L, ERBB2, PISD, KRT19, HSPB1, TRIM25, PTMA, COL18A1, CDH26, NDUFV3, PRDM15, ATP5J, and ESR1, and/or the set of target genes of the HH pathway further includes at least one target gene selected from the group consisting of: BCL2, FOXA2, FOXF1, H19, HHIP, IL1R2, JAG2, JUP, MIF, MYLK, NKX2.2, NKX2.8, PITRM1, and TOM1, and/or the set of target genes of the AR pathway further includes at least one target gene selected from the group consisting of: APP, NTS, PLAU, CDKN1A, DRG1, FGF8, IGF1, PRKACB, PTPN1, SGK1, and TACC2.

The sample(s) to be used in accordance with the present disclosure can be, e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, preferably via a biopsy procedure or other sample extraction procedure. The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, the body fluid of which a sample is extracted may be urine, gastrointestinal contents, or an extravasate. The term "extracted sample", as used herein, also encompasses the case where tissue and/or cells and/or body fluid of the subject have been taken from the subject and, e.g., have been put on a microscope slide, and where for performing the claimed method a portion of this sample is extracted, e.g., by means of Laser Capture Microdissection (LCM), or by scraping off the cells of interest from the slide, or by fluorescence-activated cell sorting techniques.

Further preferred is a method that further comprises combining the risk score and/or at least one of the inferred activities with one or more additional risk scores obtained from one or more additional prognostic tests to obtain a combined risk score, wherein the combined risk score indicates a risk that the clinical event will occur within the certain period of time. The one or more additional prognostic tests may comprise, in particular, the Oncotype DX® breast cancer test, the Mammostrat® breast cancer test, the MammaPrint® breast cancer test, the BluePrint™ breast cancer test, the CompanDx® breast cancer test, the Breast Cancer Index[SM] (HOXB13/IL17BR), the OncotypeDX® colon cancer test, and/or a proliferation test performed by measuring expression of gene/protein Ki67.

Preferentially, the clinical event is cancer, in particular, breast cancer. The risk that the clinical event will occur within the certain period of time is then preferentially the risk of return, i.e., the risk of recurrence, of cancer after treatment. This can be either local (i.e., at the side of the original tumor), or distant (i.e., metastasis, beyond the original side). Alternatively, the risk can be the risk of progression of the disease or death.

In accordance with another disclosed aspect, an apparatus comprises a digital processor configured to perform a method according to the disclosure as described herein.

In accordance with another disclosed aspect, a non-transitory storage medium stores instructions that are executable by a digital processing device to perform a method according to the disclosure as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with another disclosed aspect, a computer program comprises program code means for causing a digital processing device to perform a method according to the disclosure as described herein. The digital processing device may be a handheld device (e.g., a personal data assistant or smartphone), a notebook computer, a desktop computer, a tablet computer or device, a remote network server, or so forth.

In accordance with another disclosed aspect, a signal represents a risk score that indicates a risk that a clinical event will occur within a certain period of time, wherein the risk score results from performing a method according to the disclosure as described herein. The signal may be an analog signal or it may be a digital signal.

One advantage resides in a clinical decision support (CDS) system that is adapted to provide clinical recommendations, e.g., by deciding a treatment for a subject, based on an analysis of two or more cellular signaling pathways, for example, using a probabilistic or another mathematical model of a Wnt pathway, an ER pathway, an AR pathway and/or an HH pathway, in particular, based on a risk that a clinical event, e.g., cancer, in particular, breast cancer, will occur within a certain period of time as indicated by a risk score that is based at least in part on a combination of inferred activities of the cellular signaling pathways.

Another advantage resides in a CDS system that is adapted to assign a subject to at least one of a plurality of risk groups associated with different risks that a clinical event, e.g., cancer, in particular, breast cancer, will occur within a certain period of time as indicated by a risk score that is based at least in part on a combination of inferred activities of one or more cellular signaling pathways.

Another advantage resides in combining a risk score that indicates a risk that a clinical event will occur within a certain period of time and that is based at least in part on a combination of inferred activities of one or more cellular signaling pathways with one or more additional risk scores obtained from one or more additional prognostic tests.

The present disclosure as described herein can, e.g., also advantageously be used in connection with prognosis prediction based in part on a combination of inferred activities of one or more cellular signaling pathways, prediction of drug efficacy of e.g. chemotherapy and/or hormonal treatment based in part on a combination of inferred activities of one or more cellular signaling pathways, monitoring of drug efficacy based in part on a combination of inferred activities of one or more cellular signaling pathways, drug development based in part on a combination of inferred activities of one or more cellular signaling pathways, assay development based in part on a combination of inferred activities of one or more cellular signaling pathways, and/or cancer staging based in part on a combination of inferred activities of one or more cellular signaling pathways.

Further advantages will be apparent to those of ordinary skill in the art upon reading and understanding the attached figures, the following description and, in particular, upon reading the detailed examples provided herein below.

Figure 2A:
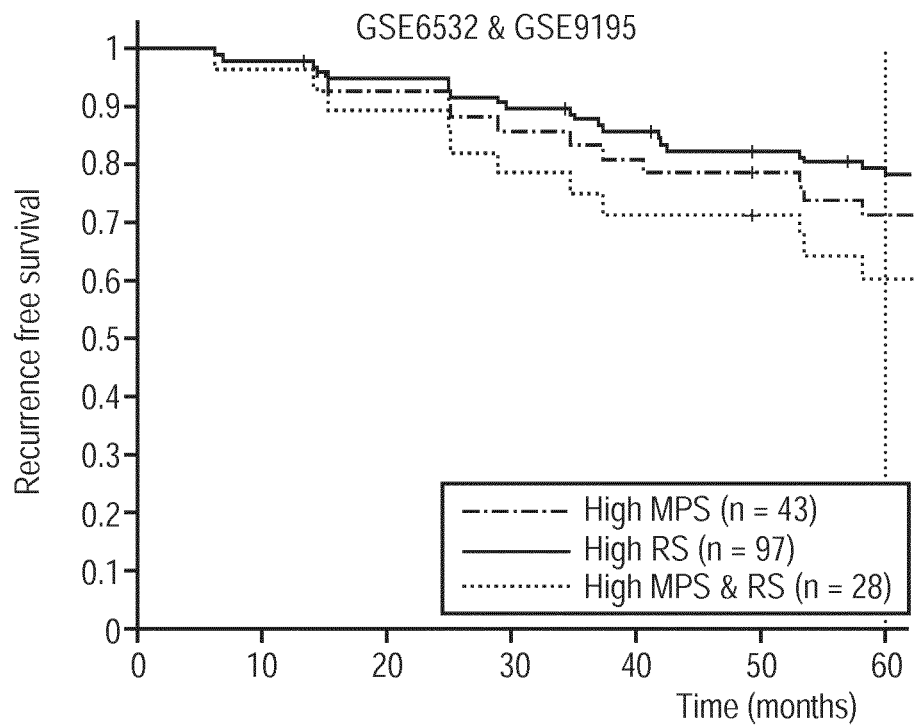
Figure 2B:
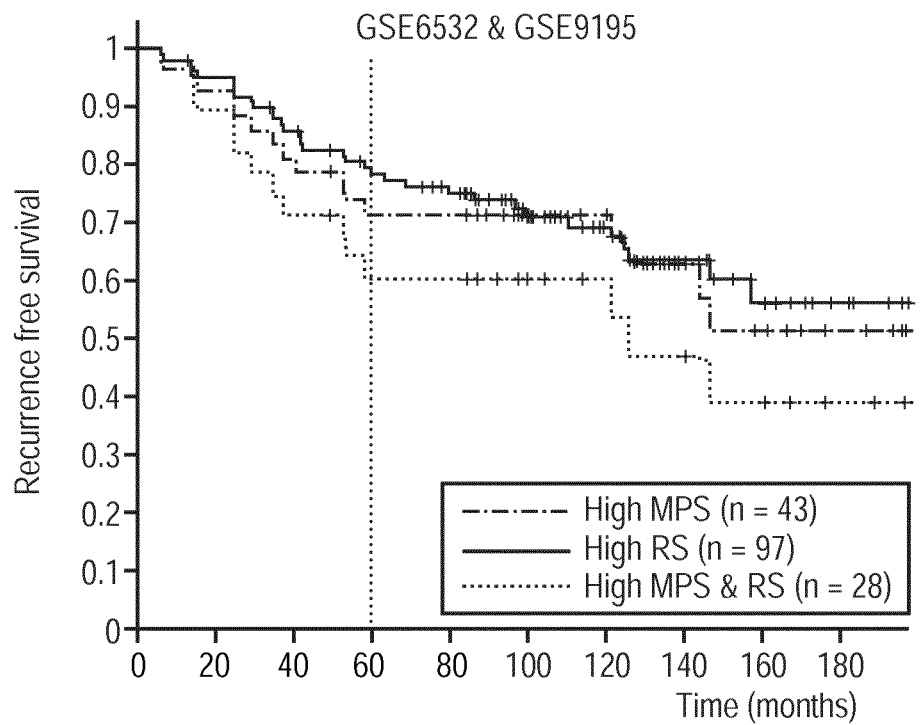

Each of FIGS. 2A and 2B shows a Kaplan-Meier plot of recurrence free survival in ER positive patients treated with surgery and adjuvant hormone treatment as reported in GSE6532 and GSE9195. Patients groups were separated based on high risk stratification based on MPS, the Oncotype DX® recurrence score (RS) and a high risk stratification for both scores (MPS & RS).

Figure 3A:
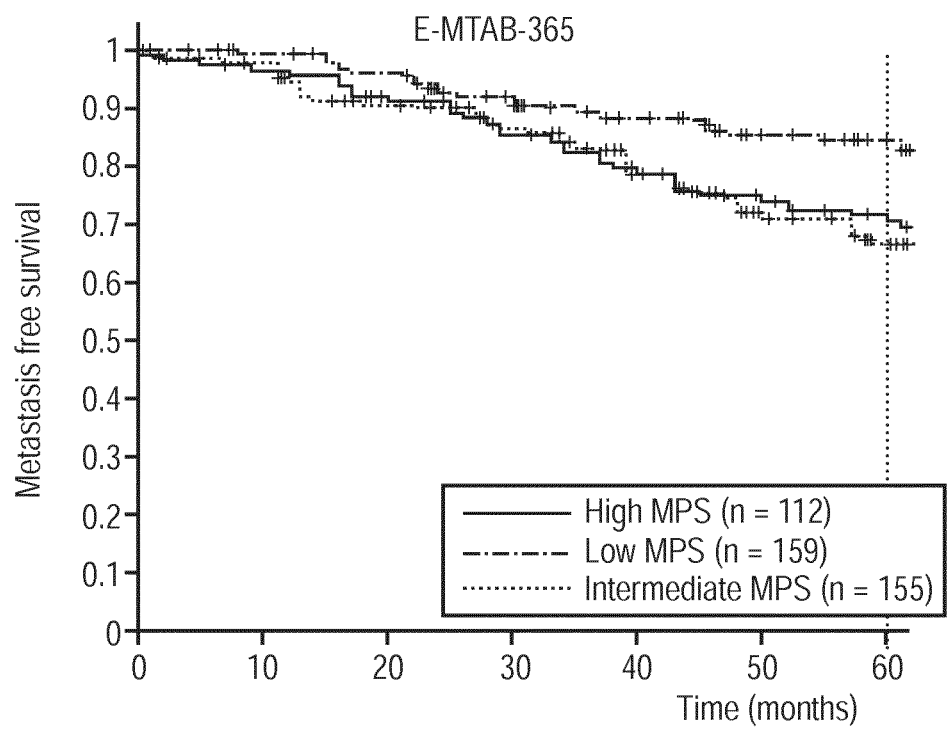
Figure 3B:
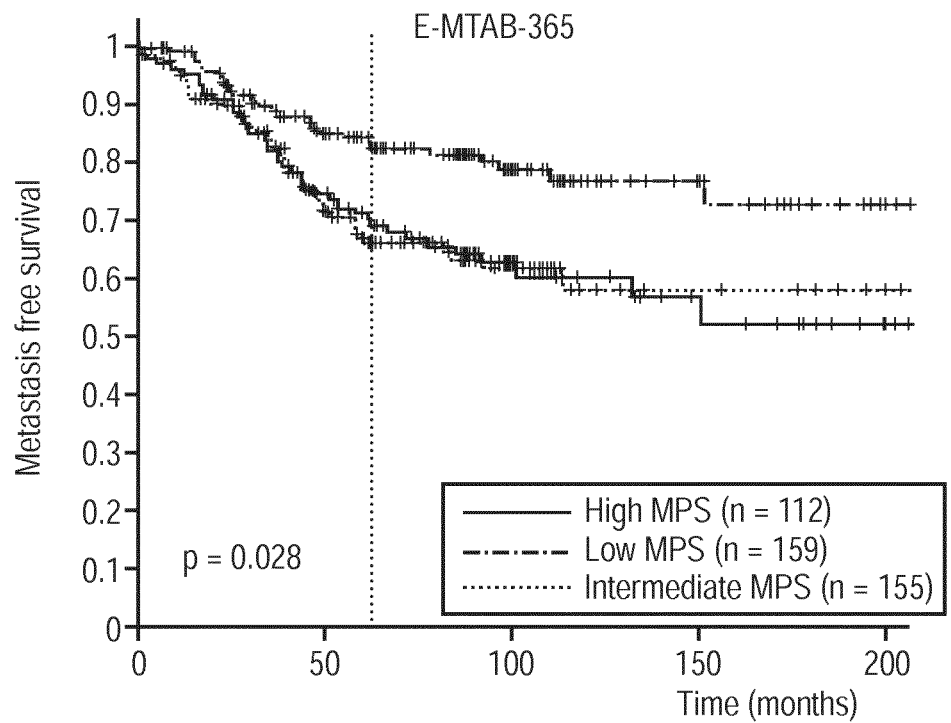

Each of FIGS. 3A and 3B shows a Kaplan-Meier plot of recurrence free survival in primary breast cancer patients as reported in E-MTAB-365. Patient groups were separated based on the risk stratification algorithm based on the multi-pathway score, as described herein. The p-value was calculated between the low risk and high risk patient groups using the log-rank test.

Figure 4A:
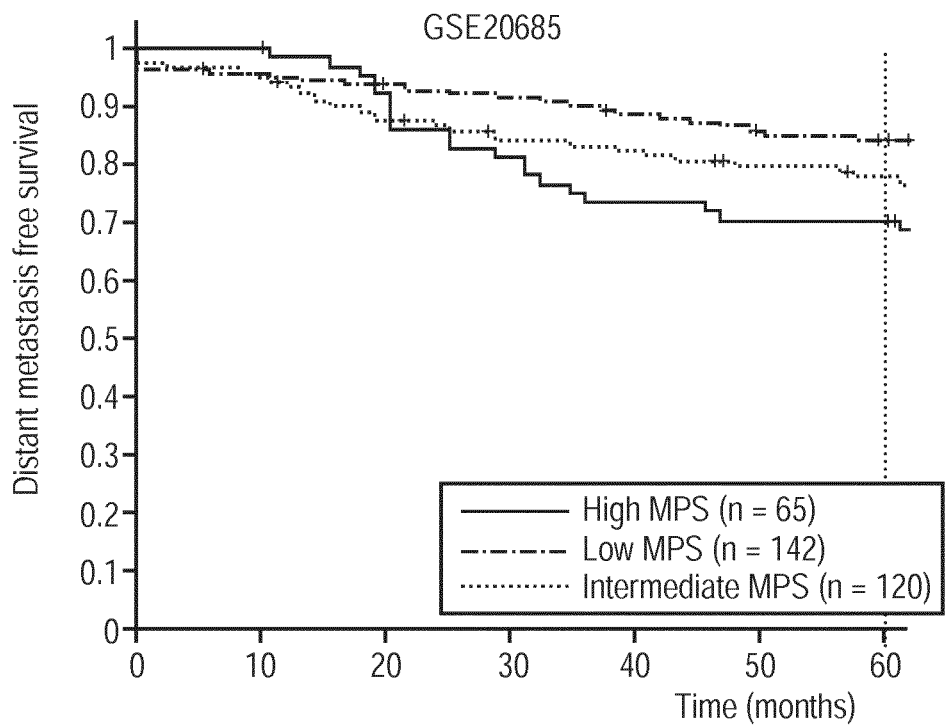
Figure 4B:
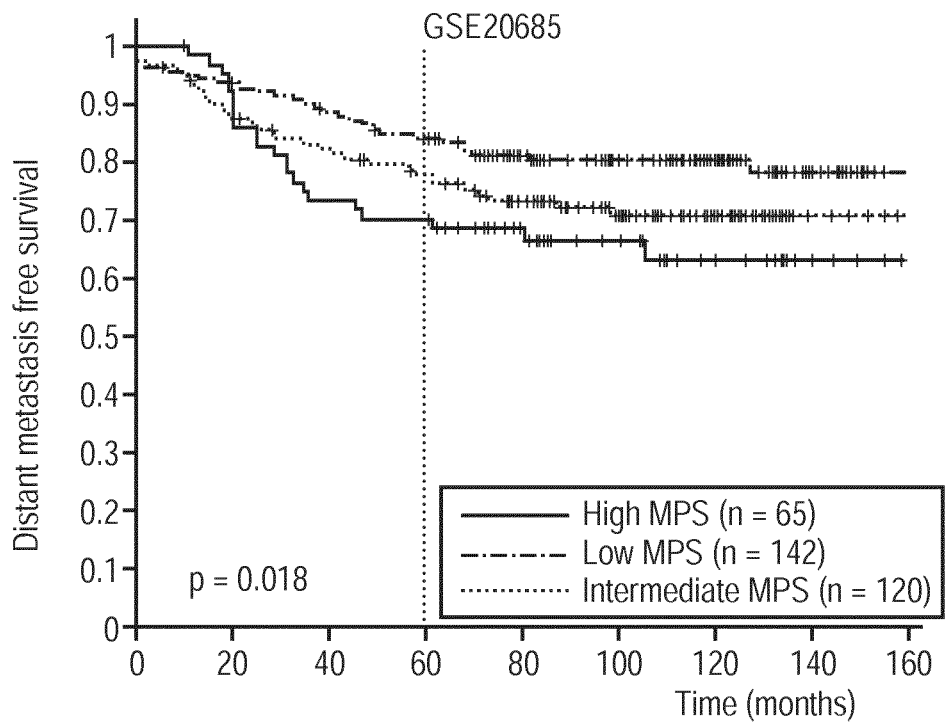

Each of FIGS. 4A and 4B shows a Kaplan-Meier plot of recurrence free survival in a diverse group of breast cancer patients as reported in GSE20685. Patients groups were separated based on the risk stratification algorithm based on the multi-pathway score provided herein. The reported p-value was calculated between the low risk and high risk patient groups using the log-rank test.

Figure 5A:
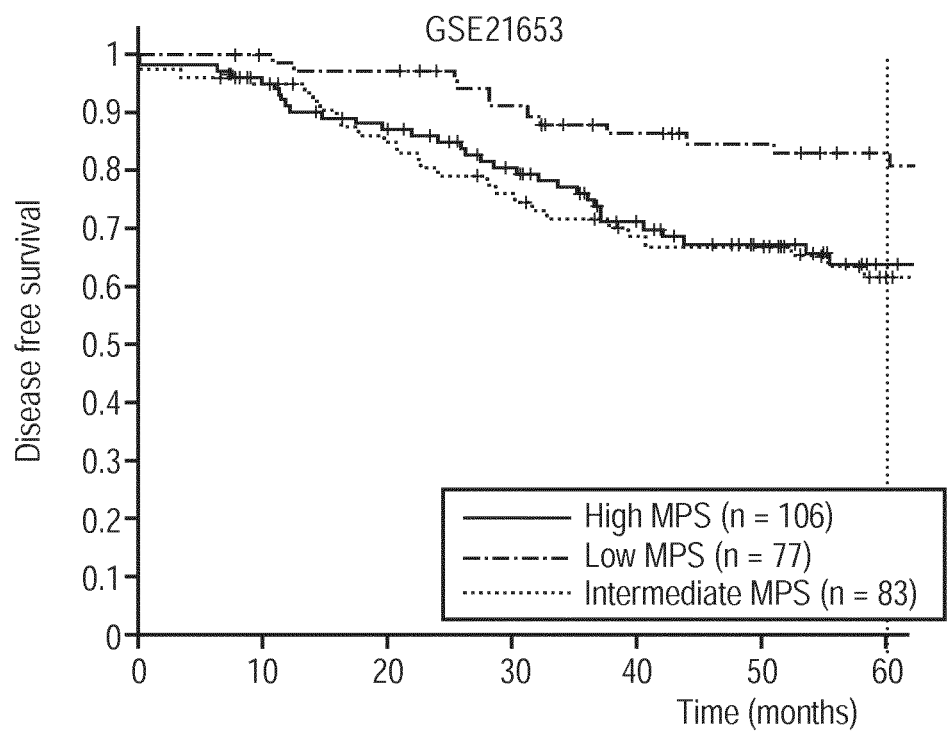
Figure 5B:
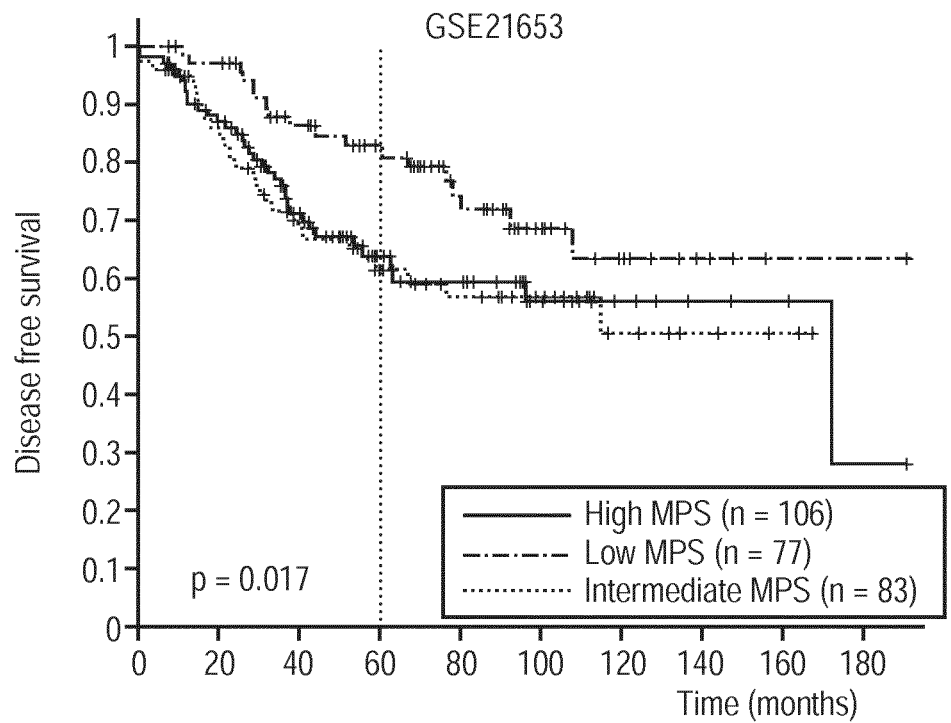

Each of FIGS. 5A and 5B shows a Kaplan-Meier plot of recurrence free survival in a group of early breast cancer patients as reported in GSE21653. Patients groups were separated based on the risk stratification algorithm based on the multi-pathway score provided herein. The reported p-value was calculated between the low risk and high risk patient groups using the log-rank test.

Figure 6:
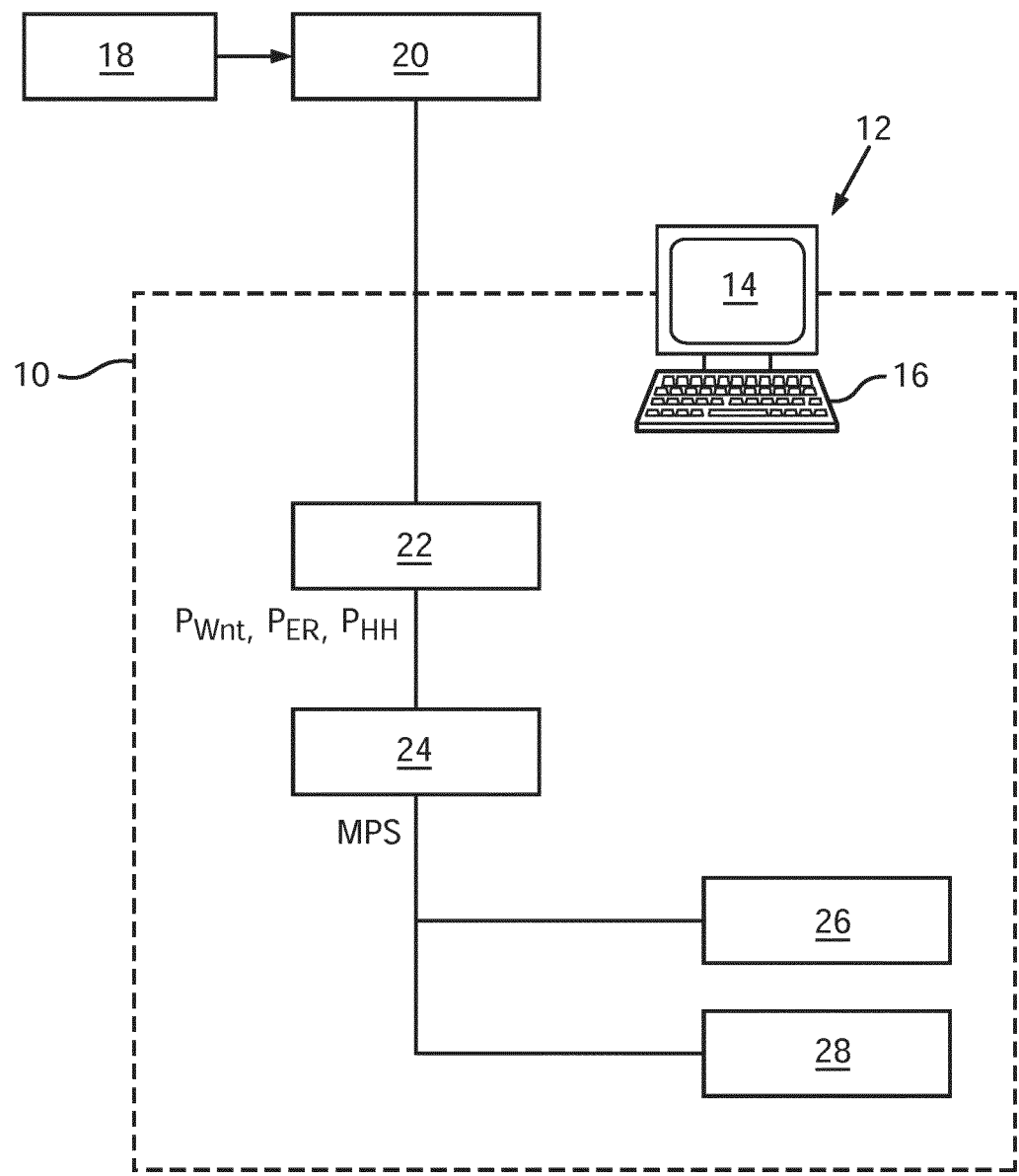

FIG. 6 diagrammatically shows a clinical decision support (CDS) system configured to determine a risk score that indicates a risk that a clinical event will occur within a certain period of time, as disclosed herein.

Figure 7:
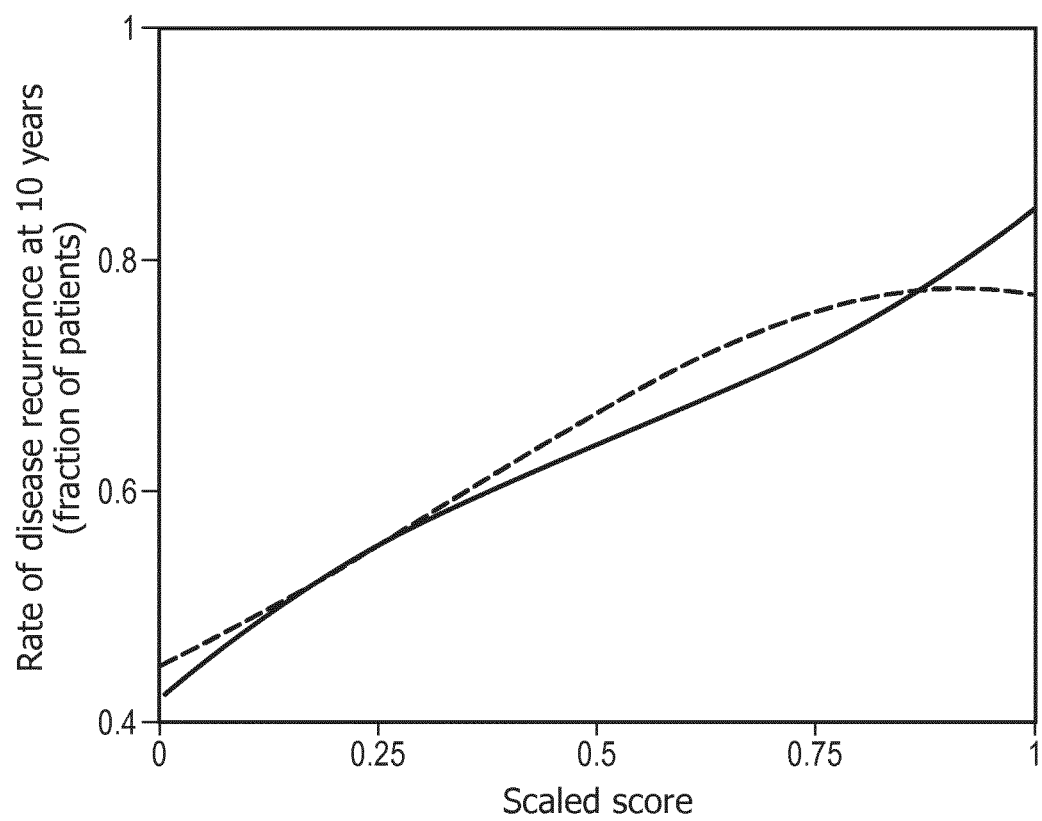

FIG. 7 shows a plot illustrating results from experiments comparing two differently determined risk scores.

DETAILED DESCRIPTION OF EMBODIMENTS

The following examples merely illustrate particularly preferred methods and selected aspects in connection therewith. The teaching provided therein may be used for constructing several tests and/or kits. The following examples are not to be construed as limiting the scope of the claims.

Example 1: Inferring Activity of Two or More Cellular Signaling Pathways

As described in detail in the published European patent application EP 2 549 399 A1 ("Assessment of Wnt pathway activity using probabilistic modeling of target gene expressions") and, in particular, in the published international patent application WO 2013/011479 A2 ("Assessment of cellular signaling pathway activity using probabilistic modeling of target gene expression"), by constructing a probabilistic model (e.g., Bayesian model) and incorporating conditional probabilistic relationships between expression levels of a number of different target genes and the activity of the cellular signaling pathway, such a model can be used to determine the activity of the cellular signaling pathway with a high degree of accuracy. Moreover, the probabilistic model can be readily updated to incorporate additional knowledge obtained by later clinical studies, by adjusting the conditional probabilities and/or adding new nodes to the model to represent additional information sources. In this way, the probabilistic model can be updated as appropriate to embody the most recent medical knowledge.

The target genes of the respective pathways may preferably be selected according to the methods described in sections "Example 3: Selection of target genes" and "Example 4: Comparison of evidence curated list and broad literature list" of WO 2013/011479 A2 and the probabilistic model may preferably be trained according to the methods described in "Example 5: Training and using the Bayesian network" of WO 2013/011479 A2. A suitable choice of the target gene(s) that are used for determining the activity of the exemplary Wnt pathway, ER pathway. AR pathway, and/or AR pathway is defined in the appended claims.

In another easy to comprehend and interpret approach described in detail in the unpublished US provisional patent application U.S. 61/745,839 resp. the unpublished international patent application PCT/IB2013/061066 ("Assessment of cellular signaling pathway activity using linear combination(s) of target gene expressions"), the activity of a certain cellular signaling pathway is determined by constructing a mathematical model (e.g., a linear or (pseudo-)linear model) incorporating relationships between expression levels of one or more target gene(s) of a cellular signaling pathway and the level of a transcription factor (TF) element, the TF element controlling transcription of the one ore more target gene(s) of the cellular signaling pathway, the model being based at least in part on one or more linear combination(s) of expression levels of the one or more target gene(s).

With respect to this later approach, the expression levels of the one or more target gene(s) may preferably be measurements of the level of mRNA, which can be the result of, e.g., (RT)-PCR and microarray techniques using probes associated with the target gene(s) mRNA sequences, and of RNA-sequencing. In another embodiment the expression levels of the one or more target gene(s) can be measured by protein levels, e.g., the concentrations of the proteins encoded by the target genes.

The aforementioned expression levels may optionally be converted in many ways that might or might not suit the application better. For example, four different transformations of the expression levels, e.g., microarray-based mRNA levels, may be:
  "continuous data", i.e., expression levels as obtained after preprocessing of microarrays using well known algorithms such as MAS5.0 and fRMA,
  "z-score", i.e., continuous expression levels scaled such that the average across all samples is 0 and the standard deviation is 1,
  "discrete", i.e., every expression above a certain threshold is set to 1 and below it to 0 (e.g., the threshold for a probeset may be chosen as the median of its value in a set of a number of positive and the same number of negative clinical samples),
  "fuzzy", i.e., the continuous expression levels are converted to values between 0 and 1 using a sigmoid function of the following format: $1/(1+\exp((thr-expr)/se))$, with expr being the continuous expression levels, thr being the threshold as mentioned before and se being a softening parameter influencing the difference between 0 and 1.

One of the simplest models that can be constructed is a model having a node representing the transcription factor (TF) element in a first layer and weighted nodes representing direct measurements of the target gene(s) expression intensity levels, e.g., by one probeset that is particularly highly correlated with the particular target gene, e.g., in microarray or (q)PCR experiments, in a second layer. The weights can be based either on calculations from a training data set or based on expert knowledge. This approach of using, in the case where possibly multiple expression levels are measured per target gene (e.g., in the case of microarray experiments, where one target gene can be measured with multiple probesets), only one expression level per target gene is particularly simple. A specific way of selecting the one expression level that is used for a particular target gene is to use the expression level from the probeset that is able to separate active and passive samples of a training data set the best. One method to determine this probeset is to perform a statistical test, e.g., the t-test, and select the probeset with the lowest p-value. The training data set's expression levels of the probe with the lowest p-value is by definition the probe with the least likely probability that the expression levels of the (known) active and passive samples overlap. Another selection method is based on odds-ratios. In such a model, one or more expression level(s) are provided for each of the one or more target gene(s) and the one or more linear combination(s) comprise a linear combination including for each of the one or more target gene(s) a weighted term, each weighted term being based on only one expression level of the one or more expression level(s) provided for the respective target gene. If the only one expression level is chosen per target gene as described above, the model may be called a "most discriminant probesets" model.

In an alternative to the "most discriminant probesets" model, it is possible, in the case where possibly multiple expression levels are measured per target gene, to make use of all the expression levels that are provided per target gene. In such a model, one or more expression level(s) are provided for each of the one or more target gene(s) and the one or more linear combination(s) comprise a linear combination of all expression levels of the one or more expression level(s) provided for the one or more target gene(s). In other words, for each of the one or more target gene(s), each of the one or more expression level(s) provided for the respective target gene may be weighted in the linear combination by its own (individual) weight. This variant may be called an "all probesets" model. It has an advantage of being relatively simple while making use of all the provided expression levels.

Both models as described above have in common that they are what may be regarded as "single-layer" models, in which the level of the TF element is calculated based on a linear combination of expression levels.

After the level of the TF element has been determined by evaluating the respective model, the determined TF element level can be thresholded in order to infer the activity of the cellular signaling pathway. A method to calculate such an appropriate threshold is by comparing the determined TF element level wlc of training samples known to have a passive pathway and training samples with an active pathway. A method that does so and also takes into account the variance in these groups is given by using a threshold $$thr = \frac{\sigma_{wlc_{pas}}\mu_{wlc_{act}} + \sigma_{wlc_{act}}\mu_{wlc_{pas}}}{\sigma_{wlc_{pas}} + \sigma_{wlc_{act}}} \quad (1)$$

where $\sigma$ and $\mu$ are the standard deviation and the mean of the training samples. In case only a small number of samples are available in the active and/or passive training samples, a pseudocount may be added to the calculated variances based on the average of the variances of the two groups:

$$\tilde{v} = \frac{v_{wlc_{act}} + v_{wlc_{pas}}}{2} \quad (2)$$

$$\tilde{v}_{wlc_{act}} = \frac{x\tilde{v} + (n_{act} - 1)v_{wlc_{act}}}{x + n_{act} - 1}$$

$$\tilde{v}_{wlc_{pas}} = \frac{x\tilde{v} + (n_{pas} - 1)v_{wlc_{pas}}}{x + n_{pas} - 1}$$

where v is the variance of the groups and x a positive pseudocount. The standard deviation σ can next be obtained by taking the square root of the variance v.

The threshold can be subtracted from the determined level of the TF element wlc for ease of interpretation, resulting in the cellular signaling pathway's activity score, such that negative values corresponds to a passive cellular signaling pathway and positive values to an active cellular signaling pathway.

As an alternative to the described "single-layer" models, a "two-layer" model representing the experimental determination of active signaling of a pathway can be used. For every target gene a summary level is calculated using a linear combination based on the measured intensities of its associated probesets ("first (bottom) layer"). The calculated summary value is subsequently combined with the summary values of the other target genes of the pathway using a further linear combination ("second (upper) layer"). The weights can be either learned from a training data set or based on expert knowledge or a combination thereof. Phrased differently, in the "two-layer" model, one or more expression level(s) are provided for each of the one or more target gene(s) and the one or more linear combination(s) comprise for each of the one or more target gene(s) a first linear combination of all expression levels of the one or more expression level(s) provided for the respective target gene ("first (bottom) layer"). The model is further based at least in part on a further linear combination including for each of the one or more target gene(s) a weighted term, each weighted term being based on the first linear combination for the respective target gene ("second (upper) layer").

The calculation of the summary values can, in a preferred version of the "two-layer" model, include defining a threshold for each target gene using the training data and subtracting the threshold from the calculated linear combination, yielding the gene summary. Here the threshold may be chosen such that a negative gene summary level corresponds with a downregulated target gene and that a positive gene summary level corresponds with an upregulated target gene. Also, it is possible that the gene summary values are transformed using e.g. one of the above-mentioned transformations (fuzzy, discrete, etc.) before they are combined in the "second (upper) layer".

After the level of the TF element has been determined by evaluating the "two-layer" model, the determined TF element level can be thresholded in order to infer the activity of the cellular signaling pathway, as described above.

In the following, the models described above with reference to U.S. 61/745,839 resp. PCT/IB2013/061066 are collectively denoted as "(pseudo-) linear models."

The target genes of the respective pathways may preferably be selected according to the methods described in sections "Example 2: Selection of target genes" and "Example 3: Comparison of evidence curated list and broad literature list" of U.S. 61/745,839 resp. PCT/IB2013/061066 and the mathematical model may preferably be trained according to the methods described in "Example 4: Training and using the mathematical model" of U.S. 61/745,839 resp. PCT/IB2013/061066. The choice of the target gene(s) defined in the appended claims is also useful for determining the activity of the exemplary Wnt pathway, ER pathway. AR pathway, and/or AR pathway with this later approach.

In the following, the selection of the target genes of the respective pathways according to the methods described in sections "Example 2: Selection of target genes" and "Example 3: Comparison of evidence curated list and broad literature list" of U.S. 61/745,839 resp. PCT/IB2013/061066 and the training of the mathematical model according to the methods described in "Example 4: Training and using the mathematical model" of U.S. 61/745,839 resp. PCT/IB2013/061066 are briefly summarized Selection of target genes according to Example 2 of U.S. 61/745,839 resp. PCT/IB2013/061066

A transcription factor (TF) is a protein complex (that is, a combination of proteins bound together in a specific structure) or a protein that is able to regulate transcription from target genes by binding to specific DNA sequences, thereby controlling the transcription of genetic information from DNA to mRNA. The mRNA directly produced due to this action of the transcription complex is herein referred to as a "direct target gene" Pathway activation may also result in more secondary gene transcription, referred to as "indirect target genes". In the following, (pseudo-)linear models comprising or consisting of direct target genes, as direct links between pathway activity and mRNA level, are preferred, however the distinction between direct and indirect target genes is not always evident. Here a method to select direct target genes using a scoring function based on available literature data is presented. Nonetheless, accidental selection of indirect target genes cannot be ruled out due to limited information and biological variations and uncertainties.

Specific pathway mRNA target genes were selected from the scientific literature, by using a ranking system in which scientific evidence for a specific target gene was given a rating, depending on the type of scientific experiments in which the evidence was accumulated. While some experimental evidence is merely suggestive of a gene being a target gene, like for example a mRNA increasing on an microarray of an embryo in which it is known that the HH pathway is active, other evidence can be very strong, like the combination of an identified pathway transcription factor binding site and retrieval of this site in a chromatin immunoprecipitation (ChIP) assay after stimulation of the specific pathway in the cell and increase in mRNA after specific stimulation of the pathway in a cell line.

Several types of experiments to find specific pathway target genes can be identified in the scientific literature, such as (but not limited to):

1. ChIP experiments in which direct binding of a pathway-transcription factor to its binding site on the genome is shown. Example: By using chromatin-immunoprecipitation (ChIP) technology subsequently putative functional TCF4 transcription factor binding sites in the DNA of colon cell lines with and without active Wnt pathway were identified, as a subset of the binding sites recognized purely based on nucleotide sequence. Putative functionality was identified as ChIP-derived evidence that the transcription factor was found to bind to the DNA binding site.
2. Electrophoretic Mobility Shift (EMSA) assays which show in vitro binding of a transcription factor to a fragment of DNA containing the binding sequence. Compared to ChIP-based evidence EMSA-based evidence is less strong, since it cannot be translated to the in vivo situation.
3. Stimulation of the pathway and measuring mRNA profiles on a microarray or using RNA sequencing, using pathway-inducible cell lines and measuring mRNA profiles measured several time points after induction—in the presence of cycloheximide, which inhibits translation to protein, thus the induced mRNAs are assumed to be direct target genes.
4. Similar to 3, but using quantitative PCR to measure the amounts of mRNAs.
5. Identification of transcription factor binding sites in the genome using a bioinformatics approach. Example for the Wnt pathway: Using the known TCF4-beta catenin transcription factor DNA binding sequence, a software program was run on the human genome sequence, and potential binding sites were identified, both in gene promoter regions and in other genomic regions.
6. Similar as 3, only in the absence of cycloheximide.
7. Similar to 4, only in the absence of cycloheximide.
8. mRNA expression profiling of specific tissue or cell samples of which it is known that the pathway is active, however in absence of the proper negative control condition.

In the simplest form one can give every potential target mRNA 1 point for each of these experimental approaches in which the target mRNA was identified.

Alternatively, points can be given incrementally, meaning one technology 1 point, second technology adds a second point, and so on. Using this relatively ranking strategy, one can make a list of most reliable target genes.

Alternatively, ranking in another way can be used to identify the target genes that are most likely to be direct target genes, by giving a higher number of points to the technology that provides most evidence for an in vivo direct target gene, in the list above this would mean 8 points for experimental approach 1), 7 to 2), and going down to one point for experimental approach 8. Such a list may be called "general target gene list".

Despite the biological variations and uncertainties, the inventors assumed that the direct target genes are the most likely to be induced in a tissue-independent manner. A list of these target genes may be called "evidence curated target gene list". These curated target lists have been used to construct computational models that can be applied to samples coming from different tissue and/or cell sources.

The "general target gene list" probably contains genes that are more tissue specific, and can be potentially used to optimize and increase sensitivity and specificity of the model for application at samples from a specific tissue, like breast cancer samples.

The following will illustrate exemplary how the selection of an evidence curated target gene list specifically was constructed for the ER pathway.

For the purpose of selecting ER target genes used as input for the (pseudo-)linear models described herein, the following three criteria were used:
1. Gene promoter/enhancer region contains an estrogen response element (ERE) motif:
    a. The ERE motif should be proven to respond to estrogen, e.g., by means of a transient transfection assay in which the specific ERE motif is linked to a reporter gene, and
    b. The presence of the ERE motif should be confirmed by, e.g., an enriched motif analysis of the gene promoter/enhancer region.
2. ER (differentially) binds in vivo to the promoter/enhancer region of the gene in question, demonstrated by, e.g., a ChIP/CHIP experiment or a chromatin immunoprecipitation assay:
    a. ER is proven to bind to the promoter/enhancer region of the gene when the ER pathway is active, and
    b. (preferably) does not bind (or weakly binds) to the gene promoter/enhancer region of the gene if the ER pathway is not active.
3. The gene is differentially transcribed when the ER pathway is active, demonstrated by, e.g.,
    a. fold enrichment of the mRNA of the gene in question through real time PCR, or microarray experiment, or
    b. the demonstration that RNA Pol II binds to the promoter region of the gene through an immunoprecipitation assay.

The selection was done by defining as ER target genes the genes for which enough and well documented experimental evidence was gathered proving that all three criteria mentioned above were met. A suitable experiment for collecting evidence of ER differential binding is to compare the results of, e.g., a ChIP/CHIP experiment in a cancer cell line that responds to estrogen (e.g., the MCF-7 cell line), when exposed or not exposed to estrogen. The same holds for collecting evidence of mRNA transcription.

The foregoing discusses the generic approach and a more specific example of the target gene selection procedure that has been employed to select a number of target genes based upon the evidence found using above mentioned approach. The lists of target genes used in the (pseudo-)linear models for exemplary pathways, namely the Wnt, ER, HH and AR pathways are shown in Table 1, Table 2. Table 3 and Table 4, respectively.

The target genes of the ER pathway used for the (pseudo-)linear models of the ER pathway described herein (shown in Table 2) contain a selection of target genes based on their literature evidence score; only the target genes with the highest evidence scores (preferred target genes according to the disclosure) were added to this short list. The full list of ER target genes, including also those genes with a lower evidence score, is shown in Table 5.

A further subselection or ranking of the target genes of the Wnt, ER, HH and AR pathways shown in Table 1, Table 2, Table 3 and Table 4 was performed based on a combination of the literature evidence score and the odds ratios calculated using the training data sets linking the probeset nodes to the corresponding target gene nodes. The odds ratios are calculated using a cutoff value, e.g. the median of all training samples if the same number of active and passive training samples are used; every value above the cutoff is declared to be high and below the cutoff low. This is done for the training samples where the pathway is known to be active or passive. Subsequently the odds ratio for a specific target gene or probeset can be calculates as follows:

$$f(\text{active,low})=n(\text{active,low})/(n(\text{active,low})+n(\text{active,high}))$$

$$f(\text{passive,low})=n(\text{passive,low})/(n(\text{passive,low})+n(\text{passive,high}))$$

$$\text{Odds ratio}=f(\text{passive,low})/(1-f(\text{passive,low}))*(1-f(\text{active,low}))/f(\text{active,low}) \quad (3)$$

With n(active, low) the number of training samples known to have an active pathway that were found to have an expression level below the cutoff, n(passive, low) the number of training samples known to have a passive pathway that were found to have an expression level below the cutoff, and so on. f(active, low) and f(passive, low) the fraction of samples known to have an active or passive pathway, respectively, and found to have an expression level below the cutoff.

Alternatively, to avoid undefined odds ratios (division by zero) one can add a for example a pseudocount to the fraction calculation, e.g.:

$$f(\text{active,low})_{pseudo}=(n(\text{active,low})+1)/(n(\text{active,low})+n(\text{active,high})+2)$$

$$f(\text{passive,low})_{pseudo}=(n(\text{passive,low})+1)/(n(\text{passive,low})+n(\text{passive,high})+2) \quad (4)$$

Alternatively, one can also replace the absolute number of samples exhibiting a probative activity by assuming some uncertainty (noise) in the measurement setting and calculate for each training sample a probability of being either "low" or "high" assuming e.g. a normal distribution (called "soft evidence"). Subsequently, the fraction calculations can be calculated following the aforementioned calculations.

$$f(\text{active,low})_{soft}=(\Sigma p(\text{active,low})+1)/(\Sigma p(\text{active,low})+\Sigma p(\text{active,high})+2)$$

$$f(\text{passive,low})_{soft}=(\Sigma p(\text{passive,low})+1)/(\Sigma p(\text{passive,low})+\Sigma p(\text{passive,high})+2) \quad (5)$$

With p(active, low) and p(passive, low) the probability for each sample that the observation is below the cutoff, assuming a standard distribution with the mean equal to the measured expression level of the respective training sample and a standard deviation equal to an estimation of the uncertainty associated with the expression level measurement, e.g. 0.25 on a log 2 scale. These probabilities are summed up over all the training samples, and next the pseudocount is added.

The odds ratio is an assessment of the importance of the target gene in inferring activity of the pathways. In general, it is expected that the expression level of a target gene with a higher odds ratio is likely to be more informative as to the overall activity of the pathway as compared with target genes with lower odds ratios. However, because of the complexity of cellular signaling pathways it is to be understood that more complex interrelationships may exist between the target genes and the pathway activity—for example, considering expression levels of various combinations of target genes with low odds ratios may be more probative than considering target genes with higher odds ratios in isolation. In Wnt, ER, HH and AR modeling reported herein, it has been found that the target genes shown in Table 6, Table 7, Table 8 and Table 9 are of a higher probative nature for predicting the Wnt, ER, HH and AR pathway activities as compared with the lower-ranked target genes (thus, the target genes shown in Tables 6 to 9 are particularly preferred according to the present disclosure). Nonetheless, given the relative ease with which acquisition technology such as microarrays can acquire expression levels for large sets of genes, it is contemplated to utilize some or all of the target genes of Table 6, Table 7, Table 8 and Table 9, and to optionally additionally use one, two, some, or all of the additional target genes of ranks shown in Table 1, Table 2, Table 3 and Table 4, in the described (pseudo-)linear models.

TABLE 1

Evidence curated list of target genes of the Wnt pathway used in the (pseudo-) linear models and associated probesets used to measure the mRNA expression level of the target genes.

| Target gene | Probeset | Target gene | Probeset |
|---|---|---|---|
| ADRA2C | 206128_at | HNF1A | 210515_at |
| ASCL2 | 207607_at | | 216930_at |
| | 229215_at | IL8 | 202859_x_at |
| AXIN2 | 222695_s_at | | 211506_s_at |
| | 222696_at | KIAA1199 | 1554685_a_at |
| | 224176_s_at | | 212942_s_at |
| | 224498_x_at | KLF6 | 1555832_s_at |
| BMP7 | 209590_at | | 208960_s_at |
| | 209591_s_at | | 208961_s_at |
| | 211259_s_at | | 211610_at |
| | 211260_at | | 224606_at |
| CCND1 | 208711_s_at | LECT2 | 207409_at |
| | 208712_at | LEF1 | 210948_s_at |
| | 214019_at | | 221557_s_at |
| CD44 | 1557905_s_at | | 221558_s_at |
| | 1565868_at | LGR5 | 210393_at |
| | 204489_s_at | | 213880_at |
| | 204490_s_at | MYC | 202431_s_at |
| | 209835_x_at | | 244089_at |
| | 210916_s_at | NKD1 | 1553115_at |
| | 212014_x_at | | 229481_at |
| | 212063_at | | 232203_at |
| | 216056_at | OAT | 201599_at |
| | 217523_at | PPARG | 208510_s_at |
| | 229221_at | REG1B | 205886_at |
| | 234411_x_at | RNF43 | 218704_at |
| | 234418_x_at | SLC1A2 | 1558009_at |
| COL18A1 | 209081_s_at | | 1558010_s_at |
| | 209082_s_at | | 208389_s_at |
| DEFA6 | 207814_at | | 225491_at |
| DKK1 | 204602_at | SOX9 | 202935_s_at |
| EPHB2 | 209588_at | | 202936_s_at |
| | 209589_s_at | SP5 | 235845_at |
| | 210651_s_at | TBX3 | 219682_s_at |
| | 211165_x_at | | 222917_s_at |
| EPHB3 | 1438_at | | 225544_at |
| | 204600_at | | 229576_s_at |
| FAT1 | 201579_at | TCF7L2 | 212759_s_at |
| FZD7 | 203705_s_at | | 212761_at |
| | 203706_s_at | | 212762_s_at |
| GLUL | 200648_s_at | | 216035_x_at |
| | 215001_s_at | | 216037_x_at |
| | 217202_s_at | | 216511_s_at |
| | 217203_at | | 236094_at |
| | 242281_at | TDGF1 | 206286_s_at |
| | | ZNRF3 | 226360_at |

TABLE 2

Evidence curated list of target genes of the ER pathway used in the (pseudo-) linear models and associated probesets used to measure the mRNA expression level of the target genes. The "most discriminative probesets" are marked by underlining.

| Target gene | Probeset | Target gene | Probeset |
|---|---|---|---|
| AP1B1 | <u>205423_at</u> | RARA | 1565358_at |
| ATP5J | <u>202325_s_at</u> | | 203749_s_at |

TABLE 2-continued

Evidence curated list of target genes of the ER pathway used in the (pseudo-) linear models and associated probesets used to measure the mRNA expression level of the target genes. The "most discriminative probesets" are marked by underlining.

| Target gene | Probeset | Target gene | Probeset |
|---|---|---|---|
| COL18A1 | 209081_s_at | | 203750_s_at |
| | <u>209082_s_at</u> | | 211605_s_at |
| COX7A2L | 201256_at | | 216300_x_at |
| CTSD | <u>200766_at</u> | SOD1 | 200642_at |
| DSCAM | 211484_s_at | TFF1 | <u>205009_at</u> |
| | 237268_at | TRIM25 | 206911_at |
| | <u>240218_at</u> | | 224806_at |
| EBAG9 | 204274_at | XBP1 | <u>200670_at</u> |
| | <u>204278_s_at</u> | | 242021_at |
| ESR1 | 205225_at | GREB1 | 205862_at |
| | <u>211233_x_at</u> | | 210562_at |
| | 211234_x_at | | 210855_at |
| | 211235_s_at | IGFBP4 | <u>201508_at</u> |
| | 211627_x_at | MYC | <u>202431_s_at</u> |
| | 215551_at | | 244089_at |
| | 215552_s_at | SGK3 | 227627_at |
| | 217163_at | | 220038_at |
| | 217190_x_at | WISP2 | <u>205792_at</u> |
| | 207672_at | ERBB2 | <u>210930_s_at</u> |
| HSPB1 | 201841_s_at | | 216836_s_at |
| KRT19 | <u>201650_at</u> | | 234354_x_at |
| | <u>228491_at</u> | CA12 | 203963_at |
| NDUFV3 | 226209_at | | <u>204508_s_at</u> |
| | 226616_s_at | | 204509_at |
| NRIP1 | <u>202599_s_at</u> | | 210735_s_at |
| | <u>202600_s_at</u> | | 214164_x_at |
| PGR | 208305_at | | 215867_x_at |
| | <u>228554_at</u> | | 241230_at |
| PISD | 202392_s_at | CDH26 | 232306_at |
| PRDM15 | <u>230553_at</u> | | 233391_at |
| | 230777_s_at | | 233662_at |
| | <u>231931_at</u> | | 233663_s_at |
| | <u>234524_at</u> | CELSR2 | 204029_at |
| | 236061_at | | <u>36499_at</u> |
| PTMA | 200772_x_at | | |
| | 200773_x_at | | |
| | 208549_x_at | | |
| | 211921_x_at | | |

TABLE 3

Evidence curated list of target genes of the HH pathway used in the (pseudo-) linear models and associated probesets used to measure the mRNA expression level of the target genes.

| Target gene | Probeset | Target gene | Probeset |
|---|---|---|---|
| GLI1 | 206646_at | CTSL1 | 202087_s_at |
| PTCH1 | 1555520_at | TCEA2 | 203919_at |
| | 208522_s_at | | 238173_at |
| | 209815_at | | 241428_x_at |
| | 209816_at | MYLK | 1563466_at |
| | 238754_at | | 1568770_at |
| PTCH2 | 221292_at | | 1569956_at |
| HHIP | 1556037_s_at | | 202555_s_at |
| | 223775_at | | 224823_at |
| | 230135_at | FYN | 1559101_at |
| | 237466_s_at | | 210105_s_at |
| SPP1 | 1568574_x_at | | 212486_s_at |
| | 209875_s_at | | 216033_s_at |
| TSC22D1 | 215111_s_at | PITRM1 | 205273_s_at |
| | 235315_at | | 239378_at |
| | 243133_at | CFLAR | 208485_x_at |
| | 239123_at | | 209508_x_at |
| CCND2 | 200939_s_at | | 209939_x_at |
| | 200952_s_at | | 210563_x_at |
| | 200953_s_at | | 210564_x_at |
| | 231259_s_at | | 211316_x_at |
| H19 | 224646_x_at | | 211317_x_at |
| | 224997_x_at | | 211862_x_at |

TABLE 3-continued

Evidence curated list of target genes of the HH pathway used in the (pseudo-) linear models and associated probesets used to measure the mRNA expression level of the target genes.

| Target gene | Probeset | Target gene | Probeset |
|---|---|---|---|
| IGFBP6 | 203851_at | | 214486_x_at |
| TOM1 | 202807_s_at | | 214618_at |
| JUP | 201015_s_at | | 217654_at |
| FOXA2 | 210103_s_at | | 235427_at |
| | 214312_at | | 237367_x_at |
| | 40284_at | | 239629_at |
| MYCN | 209756_s_at | | 224261_at |
| | 209757_s_at | IL1R2 | 205403_at |
| | 211377_x_at | | 211372_s_at |
| | 234376_at | S100A7 | 205916_at |
| | 242026_at | S100A9 | 203535_at |
| NKX2_2 | 206915_at | CCND1 | 208711_s_at |
| NKX2_8 | 207451_at | | 208712_at |
| RAB34 | 1555630_a_at | | 214019_at |
| | 224710_at | JAG2 | 209784_s_at |
| MIF | 217871_s_at | | 32137_at |
| GLI3 | 1569342_at | FOXM1 | 202580_x_at |
| | 205201_at | FOXF1 | 205935_at |
| | 227376_at | FOXL1 | 216572_at |
| FST | 204948_s_at | | 243409_at |
| | 207345_at | | |
| | 226847_at | | |
| BCL2 | 203684_s_at | | |
| | 203685_at | | |
| | 207004_at | | |
| | 207005_s_at | | |

TABLE 4

Evidence curated list of target genes of the AR pathway used in the (pseudo-) linear models and associated probesets used to measure the mRNA expression level of the target genes.

| Target gene | Probeset | Target gene | Probeset |
|---|---|---|---|
| ABCC4 | 1554918_a_at | LCP1 | 208885_at |
| | 1555039_a_at | LRIG1 | 211596_s_at |
| | 203196_at | | 238339_x_at |
| APP | 200602_at | NDRG1 | 200632_s_at |
| | 211277_x_at | NKX3_1 | 209706_at |
| | 214953_s_at | | 211497_x_at |
| AR | 211110_s_at | | 211498_s_at |
| | 211621_at | NTS | 206291_at |
| | 226192_at | PLAU | 205479_s_at |
| | 226197_at | | 211668_s_at |
| CDKN1A | 1555186_at | PMEPA1 | 217875_s_at |
| | 202284_s_at | | 222449_at |
| CREB3L4 | 226455_at | | 222450_at |
| DHCR24 | 200862_at | PPAP2A | 209147_s_at |
| DRG1 | 202810_at | | 210946_at |
| EAF2 | 1568672_at | PRKACB | 202741_at |
| | 1568673_s_at | | 202742_s_at |
| | 219551_at | | 235780_at |
| ELL2 | 214446_at | KLK3 | 204582_s_at |
| | 226099_at | | 204583_x_at |
| | 226982_at | PTPN1 | 202716_at |
| FGF8 | 208449_s_at | | 217686_at |
| FKBP5 | 204560_at | SGK1 | 201739_at |
| | 224840_at | TACC2 | 1570025_at |
| | 224856_at | | 1570546_a_at |
| GUCY1A3 | 221942_s_at | | 202289_s_at |
| | 227235_at | | 211382_s_at |
| | 229530_at | TMPRSS2 | 1570433_at |
| | 239580_at | | 205102_at |
| IGF1 | 209540_s_at | | 211689_s_at |
| | 209541_at | | 226553_at |
| | 209542_x_at | UGT2B15 | 207392_x_at |
| | 211577_s_at | | 216687_x_at |
| KLK2 | 1555545_at | | |
| | 209854_s_at | | |

TABLE 4-continued

Evidence curated list of target genes of the AR pathway used in the (pseudo-) linear models and associated probesets used to measure the mRNA expression level of the target genes.

| Target gene | Probeset | Target gene | Probeset |
|---|---|---|---|
| | 209855_s_at | | |
| | 210339_s_at | | |

TABLE 5

Gene symbols of the ER target genes found to have significant literature evidence (= ER target genes longlist).

| Gene symbol | Gene symbol | Gene symbol | Gene symbol |
|---|---|---|---|
| AP1B1 | SOD1 | MYC | ENSA |
| COX7A2L | TFF1 | ABCA3 | KIAA0182 |
| CTSD | TRIM25 | ZNF600 | BRF1 |
| DSCAM | XBP1 | PDZK1 | CASP8AP2 |
| EBAG9 | GREB1 | LCN2 | CCNH |
| ESR1 | IGFBP4 | TGFA | CSDE1 |
| HSPB1 | SGK3 | CHEK1 | SRSF1 |
| KRT19 | WISP2 | BRCA1 | CYP1B1 |
| NDUFV3 | ERBB2 | PKIB | FOXA1 |
| NRIP1 | CA12 | RET | TUBA1A |
| PGR | CELSR2 | CALCR | GAPDH |
| PISD | CDH26 | CARD10 | SFI1 |
| PRDM15 | ATP5J | LRIG1 | ESR2 |
| PTMA | COL18A1 | MYB | MYBL2 |
| RARA | CCND1 | RERG | |

TABLE 6

Shortlist of Wnt target genes based on literature evidence score and odds ratio.
Target gene KIAA1199
AXIN2
CD44
RNF43
MYC
TBX3
TDGF1
SOX9
ASCL2
IL8
SP5
ZNRF3
EPHB2
LGR5
EPHB3
KLF6
CCND1
DEFA6
FZD7

TABLE 7

Shortlist of ER target genes based on literature evidence score and odds ratio.
Target gene

CDH26
SGK3
PGR
GREB1
CA12
XBP1
CELSR2
WISP2
DSCAM

TABLE 7-continued

Shortlist of ER target genes based on literature evidence score and odds ratio.
Target gene

ERBB2
CTSD
TFF1
NRIP1

TABLE 8

Shortlist of HH target genes based on literature evidence score and odds ratio.
Target gene GLI1
PTCH1
PTCH2
IGFBP6
SPP1
CCND2
FST
FOXL1
CFLAR
TSC22D1
RAB34
S100A9
S100A7
MYCN
FOXM1
GLI3
TCEA2
FYN
CTSL1

TABLE 9

Shortlist of AR target genes based on literature evidence score and odds ratio.
Target gene KLK2
PMEPA1
TMPRSS2
NKX3_1
ABCC4
KLK3
FKBP5
ELL2
UGT2B15
DHCR24
PPAP2A
NDRG1
LRIG1
CREB3L4
LCP1
GUCY1A3
AR
EAF2

Comparison of evidence curated list and broad literature list according to Example 3 of U.S. 61/745,839 resp. PCT/IB2013/061066

The list of Wnt target genes constructed based on literature evidence following the procedure described herein (Table 1) is compared to another list of target genes not following above mentioned procedure. The alternative list is a compilation of genes indicated by a variety of data from various experimental approaches to be a Wnt target gene published in three public sources by renowned labs, known for their expertise in the area of molecular biology and the Wnt pathway. The alternative list is a combination of the genes mentioned in Table S3 from Hatzis et al. (Hatzis P, 2008), the text and Table S1A from de Sousa e Melo (de Sousa E Melo F, 2011) and the list of target genes collected and maintained by Roel Nusse, a pioneer in the field of Wnt signaling (Nusse, 2012). The combination of these three sources resulted in a list of 124 genes (=broad literature list, see Table 10). Here the question whether the performance in predicting Wnt activity in clinical samples by the algorithm derived from this alternative list is performing similarly or better compared to the model constructed on the basis of the existing list of genes (=evidence curated list, Table 1) is discussed.

TABLE 10

Alternative list of Wnt target genes (= broad literature list).

| Target gene | Reference | Target gene | Reference |
|---|---|---|---|
| ADH6 | de Sousa e Melo et al. | L1CAM | Nusse |
| ADRA2C | Hatzis et al. | LBH | Nusse |
| APCDD1 | de Sousa e Melo et al. | LEF1 | Hatzis et al., de Sousa e Melo et al., Nusse |
| ASB4 | de Sousa e Melo et al. | LGR5 | de Sousa e Melo et al., Nusse |
| ASCL2 | Hatzis et al., de Sousa e Melo et al. | LOC283859 | de Sousa e Melo et al. |
| ATOH1 | Nusse | MET | Nusse |
| AXIN2 | Hatzis et al., de Sousa e Melo et al., Nusse | MMP2 | Nusse |
| BIRC5 | Nusse | MMP26 | Nusse |
| BMP4 | Nusse | MMP7 | Nusse |
| BMP7 | Hatzis et al. | MMP9 | Nusse |
| BTRC | Nusse | MRPS6 | Hatzis et al. |
| BZRAP1 | de Sousa e Melo et al. | MYC | Hatzis et al., Nusse |
| SBSPON | de Sousa e Melo et al. | MYCBP | Nusse |
| CCL24 | de Sousa e Melo et al. | MYCN | Nusse |
| CCND1 | Nusse | NANOG | Nusse |
| CD44 | Nusse | NKD1 | de Sousa e Melo et al. |
| CDH1 | Nusse | NOS2 | Nusse |
| CDK6 | Hatzis et al. | NOTUM | de Sousa e Melo et al. |
| CDKN2A | Nusse | NRCAM | Nusse |
| CLDN1 | Nusse | NUAK2 | Hatzis et al. |
| COL18A1 | Hatzis et al. | PDGFB | Hatzis et al. |
| CTLA4 | Nusse | PFDN4 | Hatzis et al. |
| CYP4X1 | de Sousa e Melo et al. | PLAUR | Nusse |
| CYR61 | Nusse | POU5F1 | Nusse |
| DEFA5 | de Sousa e Melo et al. | PPARD | Nusse |
| DEFA6 | de Sousa e Melo et al. | PROX1 | de Sousa e Melo et al. |
| DKK1 | de Sousa e Melo et al., Nusse | PTPN1 | Hatzis et al. |
| DKK4 | de Sousa e Melo et al. | PTTG1 | Nusse |
| DLL1 | Nusse | REG3A | de Sousa e Melo et al. |
| DPEP1 | de Sousa e Melo et al. | REG4 | de Sousa e Melo et al. |
| EDN1 | Nusse | RPS27 | Hatzis et al. |
| EGFR | Nusse | RUNX2 | Nusse |
| EPHB2 | Hatzis et al., de Sousa e Melo et al., Nusse | SALL4 | Nusse |
| EPHB3 | Hatzis et al., Nusse | SLC1A1 | de Sousa e Melo et al. |
| ETS2 | Hatzis et al. | SLC7A5 | Hatzis et al. |
| FAT1 | Hatzis et al. | SNAI1 | Nusse |
| FGF18 | Nusse | SNAI2 | Nusse |
| FGF20 | Nusse | SNAI3 | Nusse |
| FGF9 | Nusse | SIK1 | Hatzis et al. |
| FLAD1 | Hatzis et al. | SOX17 | Nusse |
| AK122582 | Hatzis et al. | SOX2 | de Sousa e Melo et al. |
| FN1 | Nusse | SOX4 | Hatzis et al. |
| FOSL1 | Nusse | SOX9 | Nusse |
| FOXN1 | Nusse | SP5 | Hatzis et al., de Sousa e Melo et al. |
| FST | Nusse | SP8 | Hatzis et al. |
| FZD2 | de Sousa e Melo et al. | TCF3 | Nusse |
| FZD7 | Nusse | TDGF1 | Hatzis et al. |
| GAST | Nusse | TIAM1 | Nusse |
| GMDS | Hatzis et al. | TNFRSF19 | Nusse |
| GREM2 | Nusse | TNFSF11 | Nusse |
| HES6 | Hatzis et al. | TRIM29 | de Sousa e Melo et al. |
| HNF1A | Nusse | TSPAN5 | de Sousa e Melo et al. |
| ID2 | Nusse | TTC9 | de Sousa e Melo et al. |
| IL22 | de Sousa e Melo et al. | VCAN | Nusse |
| IL8 | Nusse | VEGFA | Nusse |
| IRX3 | de Sousa e Melo et al. | VEGFB | Nusse |
| IRX5 | de Sousa e Melo et al. | VEGFC | Nusse |
| ISL1 | Nusse | WNT10A | Hatzis et al. |
| JAG1 | Nusse | WNT3A | Nusse |
| JUN | Nusse | ZBTB7C | de Sousa e Melo et al. |
| KIAA1199 | de Sousa e Melo et al. | PATZ1 | Hatzis et al. |
| KLF4 | Hatzis et al. | ZNRF3 | Hatzis et al. |

The next step consisted of finding the probesets of the Affymetrix® GeneChip Human Genome U133 Plus 2.0 array that corresponds with the genes. This process was performed using the Bioconductor plugin in R and manual curation for the probesets relevance based on the UCSC genome browser, similar to the (pseudo-)linear models described herein, thereby removing e.g. probesets on opposite strands or outside gene exon regions. For two of the 124 genes there are no probesets available on this microarray-chip and therefore could not be inserted in the (pseudo-)linear model, these are LOC283859 and WNT3A. In total 287 probesets were found to correspond to the remaining 122 genes (Table 11).

TABLE 11

Probesets associated with the Wnt target genes in the broad literature gene list.

| Gene symbol | Probeset | Gene symbol | Probeset | Gene symbol | Probeset |
|---|---|---|---|---|---|
| ADH6 | 207544_s_at | FAT1 | 201579_at | PFDN4 | 205360_at |
| | 214261_s_at | FGF18 | 206987_x_at | | 205361_s_at |
| ADRA2C | 206128_at | | 211029_x_at | | 205362_s_at |
| APCDD1 | 225016_at | | 211485_s_at | PLAUR | 210845_s_at |
| ASB4 | 208481_at | | 231382_at | | 211924_s_at |
| | 217228_s_at | FGF20 | 220394_at | | 214866_at |
| | 217229_at | FGF9 | 206404_at | POU5F1 | 208286_x_at |
| | 235619_at | | 239178_at | PPARD | 208044_s_at |
| | 237720_at | FLAD1 | 205661_s_at | | 210636_at |
| | 237721_s_at | | 212541_at | | 37152_at |
| ASCL2 | 207607_at | AK122582 | 235085_at | | 242218_at |
| | 229215_at | FN1 | 1558199_at | PROX1 | 207401_at |
| ATOH1 | 221336_at | | 210495_x_at | | 228656_at |
| AXIN2 | 222695_s_at | | 211719_x_at | PTPN1 | 202716_at |
| | 222696_at | | 212464_s_at | | 217686_at |
| | 224176_s_at | | 214701_s_at | | 217689_at |
| | 224498_x_at | | 214702_at | PTTG1 | 203554_x_at |
| BIRC5 | 202094_at | | 216442_x_at | REG3A | 205815_at |
| | 202095_s_at | FOSL1 | 204420_at | | 234280_at |
| | 210334_x_at | FOXN1 | 207683_at | REG4 | 1554436_a_at |
| BMP4 | 211518_s_at | FST | 204948_s_at | | 223447_at |
| BMP7 | 209590_at | | 207345_at | RPS27 | 200741_s_at |
| | 209591_s_at | | 226847_at | RUNX2 | 216994_s_at |
| | 211259_s_at | FZD2 | 210220_at | | 221282_x_at |
| | 211260_at | | 238129_s_at | | 232231_at |
| BTRC | 1563620_at | FZD7 | 203705_s_at | | 236858_s_at |
| | 204901_at | | 203706_s_at | | 236859_at |
| | 216091_s_at | GAST | 208138_at | SALL4 | 229661_at |
| | 222374_at | GMDS | 204875_s_at | SLC1A1 | 206396_at |
| | 224471_s_at | | 214106_s_at | | 213664_at |
| BZRAP1 | 205839_s_at | GREM2 | 220794_at | SLC7A5 | 201195_s_at |
| SBSPON | 214725_at | | 235504_at | SNAI1 | 219480_at |
| | 235209_at | | 240509_s_at | SNAI2 | 213139_at |
| | 235210_s_at | HES6 | 226446_at | SNAI3 | 1560228_at |
| CCL24 | 221463_at | | 228169_s_at | SIK1 | 208078_s_at |
| CCND1 | 208711_s_at | HNF1A | 210515_at | | 232470_at |
| | 208712_at | | 216930_at | SOX17 | 219993_at |
| | 214019_at | ID2 | 201565_s_at | | 230943_at |
| CD44 | 1557905_s_at | | 201566_x_at | SOX2 | 213721_at |
| | 204489_s_at | | 213931_at | | 213722_at |
| | 204490_s_at | IL22 | 221165_s_at | | 228038_at |
| | 209835_x_at | | 222974_at | SOX4 | 201416_at |
| | 210916_s_at | IL8 | 202859_x_at | | 201417_at |
| | 212014_x_at | | 211506_s_at | | 201418_s_at |
| | 212063_at | IRX3 | 229638_at | | 213668_s_at |
| | 217523_at | IRX5 | 210239_at | SOX9 | 202935_s_at |
| | 229221_at | ISL1 | 206104_at | | 202936_s_at |
| CDH1 | 201130_s_at | JAG1 | 209097_s_at | SP5 | 235845_at |
| | 201131_s_at | | 209098_s_at | SP8 | 237449_at |
| | 208834_x_at | | 209099_x_at | | 239743_at |
| CDK6 | 207143_at | | 216268_s_at | TCF3 | 209151_x_at |
| | 214160_at | JUN | 201464_x_at | | 209152_s_at |
| | 224847_at | | 201465_s_at | | 209153_s_at |
| | 224848_at | | 201466_s_at | | 210776_x_at |
| | 224851_at | KIAA1199 | 1554685_a_at | | 213730_x_at |
| | 231198_at | | 212942_s_at | | 213811_x_at |
| | 235287_at | KLF4 | 220266_s_at | | 215260_s_at |
| | 243000_at | | 221841_s_at | | 216645_at |
| CDKN2A | 207039_at | L1CAM | 204584_at | TDGF1 | 206286_s_at |
| | 209644_x_at | | 204585_s_at | TIAM1 | 206409_at |
| | 211156_at | LBH | 221011_s_at | | 213135_at |
| CLDN1 | 218182_s_at | LEF1 | 210948_s_at | TNFRSF19 | 223827_at |
| | 222549_at | | 221557_s_at | | 224090_s_at |
| COL18A1 | 209081_s_at | | 221558_s_at | TNFSF11 | 210643_at |
| | 209082_s_at | LGR5 | 210393_at | | 211153_s_at |
| CTLA4 | 221331_x_at | | 213880_at | TRIM29 | 202504_at |
| | 231794_at | MET | 203510_at | | 211001_at |

TABLE 11-continued

Probesets associated with the Wnt target genes in the broad literature gene list.

| Gene symbol | Probeset | Gene symbol | Probeset | Gene symbol | Probeset |
|---|---|---|---|---|---|
|  | 234362_s_at |  | 211599_x_at |  | 211002_s_at |
|  | 236341_at |  | 213807_x_at | TSPAN5 | 209890_at |
| CYP4X1 | 227702_at |  | 213816_s_at |  | 213968_at |
| CYR61 | 201289_at | MMP2 | 1566678_at |  | 225387_at |
|  | 210764_s_at |  | 201069_at |  | 225388_at |
| DEFA5 | 207529_at | MMP26 | 220541_at | TTC9 | 213172_at |
| DEFA6 | 207814_at | MMP7 | 204259_at |  | 213174_at |
| DKK1 | 204602_at | MMP9 | 203936_s_at | VCAN | 204619_s_at |
| DKK4 | 206619_at | MRPS6 | 224919_at |  | 204620_s_at |
| DLL1 | 224215_s_at | MYC | 202431_s_at |  | 211571_s_at |
|  | 227938_s_at | MYCBP | 203359_s_at |  | 215646_s_at |
| DPEP1 | 205983_at |  | 203360_s_at |  | 221731_x_at |
| EDN1 | 218995_s_at |  | 203361_s_at | VEGFA | 210512_s_at |
|  | 222802_at | MYCN | 209756_s_at |  | 210513_s_at |
| EGFR | 1565483_at |  | 209757_s_at |  | 211527_x_at |
|  | 1565484_x_at |  | 211377_x_at |  | 212171_x_at |
|  | 201983_s_at |  | 234376_at | VEGFB | 203683_s_at |
|  | 201984_s_at | NANOG | 220184_at | VEGFC | 209946_at |
|  | 210984_x_at | NKD1 | 1553115_at | WNT10A | 223709_s_at |
|  | 211550_at |  | 229481_at |  | 229154_at |
|  | 211551_at |  | 232203_at | ZBTB7C | 217675_at |
|  | 211607_x_at | NOS2 | 210037_s_at | ZBTB7C | 227782_at |
| EPHB2 | 209588_at | NOTUM | 228649_at | PATZ1 | 209431_s_at |
|  | 209589_s_at | NRCAM | 204105_s_at |  | 211391_s_at |
|  | 210651_s_at |  | 216959_x_at |  | 210581_x_at |
|  | 211165_x_at | NUAK2 | 220987_at |  | 209494_s_at |
| EPHB3 | 1438_at | PDGFB | 204200_s_at | ZNRF3 | 226360_at |
|  | 204600_at |  | 216061_x_at |  |  |
| ETS2 | 201328_at |  | 217112_at |  |  |
|  | 201329_s_at |  |  |  |  |

Subsequently the (pseudo-)linear model was constructed similar to the described "all probesets" model using the "black and white" method to calculate the weight parameters as explained herein. Similarly to the description of the Wnt (pseudo-)linear model based on the evidence curated list, the weights associated with the edges between probesets and their respective genes, both the evidence curated list and the broad literature list, were trained using continuous fRMA processed data of 32 normal colon samples and 32 adenoma samples from data set GSE8671 from the Gene Expression Omnibus (accessible at ncbi.nlm.nih.gov/geo/, last accessed Jul. 13, 2011).

The trained (pseudo-)linear models were then tested on various data sets to infer the activity score of the Wnt pathway.

From the tests, it could be deduced that the broad literature model generally predicts more extreme activity scores for Wnt signaling being on (activity level positive) or off. In addition, the alternative model predicts similar results for the colon cancer data sets (GSE20916, GSE4183, GSE15960), but more than expected samples with predicted active Wnt signaling in breast cancer (GSE12777) and medulloblastoma sample (GSE10327) data sets.

In conclusion, the broad literature target genes list results in approximately equally well predictions of Wnt activity in colon cancer on the one hand, but worse predictions (more false positives) in other cancer types on the other hand. This might be a result of the alternative list of targets genes being too much biased towards colon cells specifically, thus too tissue specific; both de Sousa E Melo et al. and Hatzis et al. main interest was colorectal cancer although non-colon-specific Wnt target genes may be included. In addition, non-Wnt-specific target genes possibly included in these lists may be a source of the worsened predictions of Wnt activity in other cancer types. The alternative list is likely to contain more indirectly regulated target genes, which probably makes it more tissue specific. The original list is tuned towards containing direct target genes, which are most likely to represent genes that are Wnt sensitive in all tissues, thus reducing tissue specificity.

Training and using the mathematical model according to Example 4 of U.S. 61/745,839 resp. PCT/IB2013/061066

Before the (pseudo-)linear models as exemplary described herein can be used to infer pathway activity in a test sample the weights indicating the sign and magnitude of the correlation between the nodes and a threshold to call whether a node is either "absent" or present" need to be determined. One can use expert knowledge to fill in the weights and threshold a priori, but typically models are trained using a representative set of training samples, of which preferably the ground truth is known. E.g. expression data of probesets in samples with a known present transcription factor complex (=active pathway) or absent transcription factor complex (=passive pathway). However, it is impractical to obtain training samples from many different kinds of cancers, of which it is known what the activation status is of the pathway to be modeled. As a result, available training sets consist of a limited number of samples, typically from one type of cancer only. Herein a method is described to determine the parameters necessary to classify test samples as having an active or passive pathway.

Known in the field are a multitude of training algorithms (e.g. regression) that take into account the model topology and changes the model parameters, here weight and threshold, such that the model output, here weighted linear score, is optimized. Herein we demonstrate two exemplary methods that can be used to calculate the weights directly from the expression levels without the need of an optimization algorithm.

Preferably, the training of the (pseudo-)linear models of the Wnt, ER, HH and AR pathways is done using public data available on the Gene Expression Omnibus (accessible at ncbi.nlm.nih.gov/geo/, cf. above).

The first method, defined here as "black and white"-method boils down to a ternary system with the weighting factors being an element of $\{-1, 0, 1\}$. If we would put this in the biological context the $-1$ and $1$ corresponds to genes or probes that are down- and upregulated in case of pathway activity, respectively. In case a probe or gene cannot be statistically proven to be either up- or downregulated, it receives a weight of 0. Here we have used a left-sided and right-sided, two sample t-test of the expression levels of the active pathway samples versus the expression levels of the samples with a passive pathway to determine whether a probe or gene is up- or downregulated given the used training data. In cases where the average of the active samples is statistically larger than the passive samples, i.e. the p-value is below a certain threshold, e.g. 0.3, then the probeset or target gene is determined to be upregulated. Conversely, in cases where the average of the active samples is statistically lower than the passive samples this probeset or target gene is determined to be downregulated upon activation of the pathway. In case the lowest p-value (left- or right-sided) exceeds the aforementioned threshold we define the weight of this probe or gene to be 0.

In another preferred embodiment, an alternative method to come to weights and threshold(s) is used. This alternative method is based on the logarithm (e.g. base e) of the odds ratio, and therefore called "log odds"-weights. The odds ratio for each probe or gene is calculated based on the number of positive and negative training samples for which the probe/gene level is above and below a corresponding threshold, e.g. the median of all training samples (equation 3). A pseudo-count can be added to circumvent divisions by zero (equation 4). A further refinement is to count the samples above/below the threshold in a somewhat more probabilistic manner, by assuming that the probe/gene levels are e.g. normally distributed around its observed value with a certain specified standard deviation (e.g. 0.25 on a 2-log scale), and counting the probability mass above and below the threshold (equation 5).

Alternatively, one can employ optimization algorithms known in the field such as regression to determine the weights and the threshold(s) of the (pseudo-)linear models described herein.

One has to take special attention to the way the parameters are determined for the (pseudo-)linear models to generalize well. Alternatively, one can use other machine learning methods such as Bayesian networks that are known in the field to be able to generalize quite well by taking special measures during training procedures.

Preferably, the training of the (pseudo-)linear models of the Wnt, ER, HH and AR pathways is done using public data available on the Gene Expression Omnibus (accessible at ncbi.nlm.nih.gov/geo/). The models were exemplary trained using such public data.

Please note that with respect to WO 2013/011479 A2 and U.S. 61/745,839 resp. PCT/IB2013/061066, the rank order of the ER target genes defined in the appended claims is slightly changed because new literature evidence was added. The ER target genes were selected and ranked in a similar way as described in Example 3 of U.S. 61/745,839 resp. PCT/IB2013/061066. The genes were ranked by combining the literature evidence score and the individual ability of each gene to differentiate between an active and inactive pathway within the Affymetrix model. This ranking was based on a linear combination of weighted false positive and false negative rates obtained for each gene when training the model with a training set of MCF7 cell line samples, which were depleted of estrogen and subsequently remained depleted or were exposed to 1 nM estrogen for 24 hours (GSE35428), and testing the model with the training set and two other training sets in which MCF7 cells were depleted of estrogen and subsequently remained depleted or were exposed to 10 nM or 25 nM estrogen (GSE11352 and GSE8597, respectively).

(Note that a combination of weighted false positives and false negatives (instead of odds ratios) was used to account for the different experimental conditions used in the various sets. The different weights were set according with the inventor's confidence that the false positives (negatives) were a consequence of the model and not of the different experimental condition the sample had been subjected to. For example, in all experiments the MCF7 cell line samples were first depleted of estrogen for a period of time before being exposed to estrogen or further depleted for another 24 hs. A shorter depletion time could cause the pathway to still being active despite the estrogen depletion, in this case a false positive would have less weight than when both the test and training samples were depleted for the same amount of time.)

Example 2: Determining Risk Score

In general, many different formulas can be devised for determining a risk score that indicates a risk that a clinical event will occur within a certain period of time and that is based at least in part on a combination of inferred activities of two or more cellular signaling pathways in a tissue and/or cells and/or a body fluid of a subject, i.e.:

$$MPS = F(P_1, \ldots, P_N) + X, \quad (6)$$

with MPS being the risk score (the term "MPS" is used herein as an abbreviation for "Multi-Pathway Score" in order to denote that the risk score is influenced by the inferred activities of two or more cellular signaling pathways), $P_i$ being the activity score of cellular signaling pathway i, N being the total number of cellular signaling pathways under consideration, and X being a placeholder for possible further factors or parameters that may go into the equation. Such a formula may be more specifically a polynomial of a certain degree in the given variables, or a linear combination of the variables. The weighting coefficients and powers in such a polynomial may be set based on expert knowledge, but typically a training data set with known ground truth, e.g., survival data, is used to obtain estimates for the weighting coefficients and powers of equation (6). The inferred activities are combined using equation (6) and will subsequently generate an MPS. Next, the weighting coefficients and powers of the scoring function are optimized such that a high MPS correlates with a longer time period until occurrence of the clinical event and vice versa. Optimizing the scoring function's correlation with occurrence data can be done using a multitude of analysis techniques. e.g., a Cox proportional hazards test (as exemplarily used herein), a log-rank test, a Kaplan-Meier estimator in conjunction with standard optimization techniques such as gradient-descent or manual adaptation.

In this example, the clinical event is cancer, in particular, breast cancer, and the inferred activities of the Wnt pathway, the ER (Estrogen Receptor) pathway, the HH (Hedgehog) pathways, and the AR (Androgen Receptor) pathway are considered, as discussed in detail in the published international patent application WO 2013/011479 A2 ("Assessment of cellular signaling pathway activity using probabilistic modeling of target gene expression") or in the unpublished US provisional patent application U.S. 61/745,839 resp. the unpublished international patent application PCT/IB2013/061066 ("Assessment of cellular signaling pathway activity using linear combination(s) of target gene expressions").

The formula that is exemplarily used herein takes into account the activities of the Wnt pathway, the ER pathway, and the HH pathway. It is based on the inventors' observations derived from cancer biology research as well as correlations discovered in publically available datasets between survival and Wnt, ER, and HH pathway activities. Early developmental pathways, like Wnt and Hedgehog, are thought to play a role in metastasis caused by cancer cells which have reverted to a more stem cell like phenotype, called cancer stem cells. Indeed, the inventors believe that sufficient indications are available for the early developmental pathways, such as Wnt pathway, to play a role in cancer metastasis, enabling metastatic cancer cells to start dividing in the seeding location in another organ or tissue. Metastasis is associated with bad prognosis and represents a form of cancer recurrence, thus activity of early developmental pathways, such as the Wnt and HH pathway, in cancer cells is expected by the inventors to be predictive for bad prognosis, whereas passivity of the ER pathway seems to be correlated with poor outcome in breast cancer patients. The presumed role of Wnt and Hedgehog pathways in cancer progression and metastasis is based on preclinical research, and has not been shown in subjects, since no methods for measuring their activity are available.

These inventors' observations from biology research and the clinical correlations that Wnt and HH activity may play a role in cancer recurrence and ER activity seems to be linked to good clinical outcome are combined herein in the following exemplary formula $$MPS = -\alpha \cdot P_{ER} + \beta \cdot \max(P_{Wnt}, P_{HH}), \quad (7)$$

wherein $P_{ER}$, $P_{Wnt}$, and $P_{HH}$ denote the inferred activity of the ER pathway, the Wnt pathway, and the HH pathway, respectively (e.g., in the range between 0 and 1), and $\alpha$ and $\beta$ are non-negative, preferably, positive, constant scaling factors. In this example, $\alpha$ and $\beta$ are exemplarily chosen to be equal to 1 and the probabilities of the Wnt pathway, the ER pathway, and the HH pathway being in their active state have been used as inferred by the method described in detail in the published international patent application WO 2013/011479 A2 ("Assessment of cellular signaling pathway activity using probabilistic modeling of target gene expression"). The Bayesian network models of the herein used ER, Wnt, and HH pathways comprise A) a top level node of the transcription factor level of interest, B) a level of nodes representing the presence of the target genes of interest (Table 2, Table 1 and Table 3 in WO 2013/011479 A2, respectively) and C) a level of nodes representing the probesets associated with the target genes of interest (Table 2, Table 1 and Table 3 in WO 2013/011479 A2, respectively). The prior probability of the TF element being present or absent was set to 0.5. The conditional probabilities between levels A and B were carefully handpicked as described in WO 2013/011479 A2 as follows (i) TF absent/target gene down: 0.95, (ii) TF absent/target gene up: 0.05. (iii) TF present/target gene down: 0.30, and (iv) TF present/target gene up: 0.70, whereas the conditional probabilities between levels B and C were trained on data from GSE8597, GSE8671 and GSE7553, respectively.

As training data, GSE8597 has been used for the ER pathway, GSE8671 has been used for the Wnt pathway, and GSE7553 has been used for the HH pathway. The target genes that have been incorporated in the inferring were GREB1, PGR, XBP1, CA12, SOD1, CTSD, IGFBP4, TFF1, SGK3, NRIP1, CELSR2, WISP2, APIB1, RARA, MYC, DSCAM, EBAG9, COX7A2L, ERBB2, PISD, KRT19, HSPB1, TRIM25, PTMA, COL18A1, CDH26, NDUFV3, PRDM15, ATP5J, ESR1 for the ER pathway, KIAA1199, AXIN2, RNF43, TBX3, TDGF1, SOX9, ASCL2, IL8, SP5, ZNRF3, KLF6, CCND1, DEFA6, FZD7, NKD1, OAT, FAT1, LEF1, GLUL, REG1B, TCF7L2, COL18A1, BMP7, SLC1A2, ADRA2C, PPARG, DKK1, HNF1A, LECT2 for the Wnt pathway, and GLI1, PTCH1, PTCH2, IGFBP6, SPP1, CCND2, FST, FOXL1, CFLAR, TSC22D1, RAB34, S100A9, S100A7, MYCN, FOXM1, GL13, TCEA2, FYN, CTSL1, BCL2, FOXA2, FOXF1, H19, HHIP, IL1R2, JAG2, JUP, MIF, MYLK, NKX2.2, NKX2.8, PITRM1, and TOM1 for the HH pathway.

The resulting MPS ranges from −1, which signifies a low risk of recurrence of the clinical event, here cancer, either local or distant, in particular, breast cancer, within a certain period of time, to +1 for high risk recurrence patients.

Please note that while in the following, the MPS calculated according to equation (7) is used, another suitable way of calculating the risk score (MPS) based on the inferred activities of the Wnt, ER, and HH pathway is provided by the following exemplary formula:

$$MPS = -\alpha \cdot P_{ER} + \beta \cdot P_{Wnt} + \gamma \cdot P_{HH}, \quad (8)$$

wherein $P_{ER}$, $P_{Wnt}$, and $P_{HH}$ denote the inferred activity of the ER pathway, the Wnt pathway, and the HH pathway, respectively (e.g., in the range between 0 and 1), and $\alpha$, $\beta$, and $\gamma$ are non-negative constant scaling factors.

Two methods to quantize such a prognostic value exemplarily used herein are Cox's proportional hazard regression models and Kaplan-Meier plots in conjunction with the log-rank test:

The first method fits a hazard model to the survival data with one or more covariates. In short, such a hazard model explains the variation in survival (clinical event) within the population based on the (numerical) value of the covariates. As a result of the fit, each included covariate will be assigned a hazard ratio (HR) which quantifies the associated risk of the clinical event based on the covariate's value, e.g., a HR of two corresponds with a two times higher risk of the clinical event of interest for patients with an increase of one in the covariate's value. In detail, a value of HR of one means that this covariate has no impact on survival, whereas for HR<1, an increase in the covariate number signifies a lower risk and a decrease in the covariate number signifies a higher risk, and for HR>1, an increase in the covariate number signifies a higher risk and a decrease in the covariate number signifies a lower risk. Along with the hazard ratios, the 95% confidence interval and p-values are reported (i.e., the one-sided probability that the hazard ratio is significantly less or greater than one). All covariates are scaled between zero and one to make a direct comparison of hazard ratios straightforward.

The latter method involves plotting a Kaplan-Meier curve that represents the probability of surviving the clinical event as a function of time. For example, by plotting the Kaplan-Meier curves for different risk groups in the population based on an exemplary prognostic test, one can visualize the quality of the separation of risk of the exemplary clinical event. This quality can be further quantized by means of a log-rank test, which calculates the probability (p-value) that two survival functions are equal.

Figure 1:
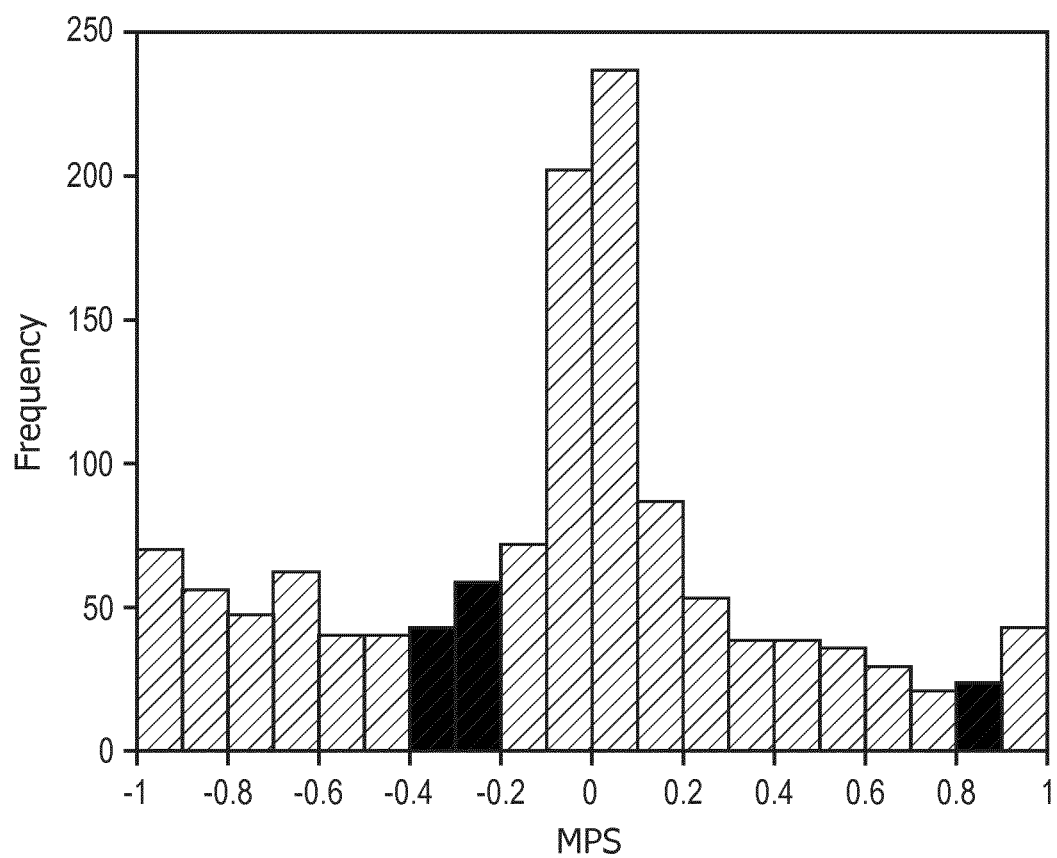
FIG. 1 shows a histogram of the MPS calculated using equation (7) with $\alpha=1$ and $\beta=1$ for a set of diverse breast cancer patients (n=1294) from GSE6532, GSE9195, GSE20685, GSE20685, GSE21653, and E-MTAB-365.

To stratify patients according to risk, the following algorithm is exemplarily used: patients that have an MPS less than −0.1 correlate with a high ER pathway activity probability and thus are designated to have a low recurrence risk, whereas an MPS greater than +0.1 is associated with a high activity of the high risk Wnt and/or HH pathway and thus correlated with a high recurrence risk. Patients with a MPS between −0.1 and +0.1 are classified as having an intermediate risk of developing a recurrence as this group includes patients with either active low risk pathway such as the ER pathway as well as activation of high risk signaling pathways such as Wnt or HH or patients in which none of the pathways were inferred to be driving tumour growth. The thresholds −0.1 and +0.1 are based on an analysis of the distribution of the resulting MPS score in a number of datasets including 1294 diverse breast cancer patients as reported in the Gene Expression Omnibus (GSE6532, GSE9195, GSE20685, GSE20685, and GSE21653 accessible at ncbi.nlm.nih.gov/geo/, last accessed Feb. 13, 2013) and ArrayExpress (E-MTAB-365, ebi.ac.uk/arrayexpress/experiments/, last accessed Feb. 13, 2013), as can be seen in FIG. 1.

As a benchmark, the separate pathway activities and the breast cancer Oncotype DX® test from Genomic Health, which was shown to be a good predictor for recurrence and to be concordant with other gene-expression-based predictors for breast cancer, were used. The Oncotype DX® test returns a risk or recurrence score (RS) between 0 and 100 that is calculated based on a combination of expression levels measured for a panel of genes. The RS is optimized with respect to 10-year survival in ER positive, HER2 negative (protein staining or FISH), node negative breast cancer patients (see Paik, S., et al.: "A multi-gene assay to predict recurrence of Tamoxifen-treated, node-negative breast cancer," The New England Journal of Medicine, 351(27), (2004), pages 2817-2826; Fan, C., et al.: "Concordance among gene-expression-based predictors for breast cancer," The New England Journal of Medicine, 355(6), (2006), pages 560-569). The RS was calculated using the microarray expression data reported in the mentioned datasets following the procedure reported by Fan et al. (see Fan, C., et al. (2006)) and patients were subsequently divided into low risk, intermediate risk, and high risk patients according to the Oncotype DX® risk stratification algorithm.

Results
(i) Erasmus Data

All 204 patients in GSE12276 from the Gene Expression Omnibus (accessible at ncbi.nlm.nih.gov/geo/, last accessed Feb. 13, 2013) suffered a relapse (median time to recurrence: 21 months, range: 0-115 months), which makes it a good dataset to investigate the prognostic value of the pathway activity scores and MPS derived thereof with respect to recurrence risk, to see if they can separate the early recurrence cases from the late cases.

Univariate Cox's proportional hazard regression models were fitted using the Wnt pathway, the ER pathway, the HH pathway, and the AR pathway, as well as normalized values (i.e., values between 0 and 1) for the RS and the MPS, see Table 12 below. The univariate analyses indicate that the RS and the MPS both have a hazard ratio significantly larger than 1, whereas $P_{ER}$ has a hazard ratio significantly smaller than 1. A multivariate analysis, which includes a combination of RS with either $P_{ER}$ or MPS, resulted in two significant predictors (p<0.05). Whereas the combination of MPS and $P_{ER}$ resulted in a loss of significance for one of the predictors (MPS: p>0.05), which is explained by the fact that $P_{ER}$ is also an element of the multi-pathway score. Consequently the multivariate analysis using RS, MPS, and $P_{ER}$ also failed logically.

TABLE 12

Cox's proportional hazard ratios of all patients in GSE12276.

|  |  | HR | HR 95% CI | | p |
|---|---|---|---|---|---|
| Univariate | RS (normalized) | 2.66 | 1.81 | 3.93 | <0.01 |
|  | $P_{Wnt}$ | 1.18 | 0.79 | 1.77 | 0.21 |
|  | $P_{ER}$ | 0.42 | 0.28 | 0.64 | <0.01 |
|  | $P_{HH}$ | 0.78 | 0.51 | 1.21 | 0.14 |
|  | $P_{AR}$ | 0.98 | 0.46 | 2.06 | 0.48 |
|  | MPS (normalized) | 2.09 | 1.26 | 3.47 | <0.01 |
| Multivariate | RS (normalized) | 2.50 | 1.68 | 3.72 | <0.01 |
|  | MPS (normalized) | 1.66 | 0.98 | 2.80 | 0.03 |
| Multivariate | RS (normalized) | 2.18 | 1.41 | 3.35 | <0.01 |
|  | $P_{ER}$ | 0.61 | 0.39 | 0.96 | 0.017 |
| Multivariate | MPS (normalized) | 0.87 | 0.40 | 1.86 | 0.35 |
|  | $P_{ER}$ | 0.39 | 0.22 | 0.71 | <0.01 |
| Multivariate | RS (normalized) | 2.22 | 1.43 | 3.46 | <0.01 |
|  | MPS (normalized) | 1.18 | 0.54 | 2.58 | 0.34 |
|  | $P_{ER}$ | 0.68 | 0.35 | 1.31 | 0.12 |

In conclusion, the univariate analyses showed that the Oncotype DX® recurrence score (RS) from Genomic Health has a stronger predictive power with respect to recurrence than the pathway-based predictors $P_{Wnt}$, $P_{HH}$, and $P_{AR}$, which is not unexpected since RS is specifically optimized to predict recurrence whereas $P_{Wnt}$, $P_{HH}$, and $P_{AR}$ are aimed to predict pathway activity. Nevertheless, $P_{ER}$ and the MPS derived thereof in combination with $P_{Wnt}$ and $P_{HH}$ are also strong, significant predictors for recurrence. In addition, combining RS with either $P_{ER}$ or MPS resulted in an improved risk stratification, outperforming the separate predictors (not significant, p≈0.14). In addition, this also implies that the Oncotype DX® recurrence score (RS) and the multi-pathway score (MPS) are complementary predictors of recurrence and both consider different mechanisms underlying tumor growth.

Taking into account only the 71 patients eligible for the Oncotype DX® breast cancer test (i.e., the patients that are ER positive and lymph node negative with an unknown HER2 status) from the same dataset, it is observed that RS and $P_{ER}$ are still strong predictors for recurrence (p<0.05); see Table 13 below. On the other hand, it is observed that MPS is not a significant predictor anymore, which is likely a result of the more homogeneous patient group (with only a few Wnt- and HH-active tumors). Strikingly, the strongest predictor for recurrence prognosis in ER positive (protein staining) and node negative patients is $P_{ER}$ and not the Oncotype DX® recurrence score (RS).

TABLE 13

Cox's proportional hazard ratios for ER positive and lymph node negative patients in GSE12276.

|  |  | HR | HR 95% CI | | p |
|---|---|---|---|---|---|
| Univariate | RS (normalized) | 1.78 | 0.98 | 3.26 | 0.03 |
|  | $P_{Wnt}$ | 0.54 | 0.25 | 1.17 | 0.058 |
|  | $P_{ER}$ | 0.48 | 0.26 | 0.89 | <0.01 |
|  | $P_{HH}$ | 0.68 | 0.32 | 1.44 | 0.16 |
|  | $P_{AR}$ | 1.40 | 0.35 | 5.69 | 0.32 |
|  | MPS (normalized) | 1.59 | 0.68 | 3.68 | 0.14 |
| Multivariate | RS (normalized) | 1.19 | 0.55 | 2.60 | 0.33 |
|  | $P_{ER}$ | 0.54 | 0.25 | 1.17 | 0.060 |

(ii) Guy's Hospital Data

The Erasmus GSE12276 dataset has a bias towards recurrence, because it only includes patients that had a recurrence during follow-up. To investigate the prognostic value of pathway-based predictions, they were applied to a more clinically relevant set of patients reported by Guy's hospital in GSE6532 and GSE9195 (164 patients in total). The patients in these datasets were diagnosed with an ER positive tumor and were treated with surgery and adjuvant hormone treatment for 5 years.

A direct comparison of the Oncotype DX® recurrence score (RS) with MPS (see Table 14) indicates that both tests are approximately equally well capable to predict recurrence risk (HR: 4.41 (1.93-10.091) vs. 6.43 (1.66-24.90)). The predictive power of both tests remains significant once combined in a multivariate analysis. This supports the results obtained in the Erasmus GSE12276 dataset; the recurrence score (RS) obtained from the Oncotype DX® breast cancer test and MPS are complementary predictors of recurrence and both consider different mechanisms underlying tumor growth. Combining these two tests further improves the recurrence free survival prediction, as can be seen in FIG. 2 (please note that FIG. 2.A shows a clipping of FIG. 2.B, zoomed in on the time axis) and Table 14 below.

TABLE 14

Cox's proportional hazard ratios of all patients in GSE6532 and GSE9195.

|  |  | HR | HR 95% CI |  | p |
|---|---|---|---|---|---|
| Univariate | RS (normalized) | 4.41 | 1.93 | 10.09 | <0.01 |
|  | MPS (normalized) | 6.43 | 1.66 | 24.90 | <0.01 |
| Multivariate | RS (normalized) | 3.99 | 1.71 | 9.29 | <0.01 |
|  | MPS | 4.57 | 1.19 | 17.47 | 0.026 |

(iii) Cartes d'Identité Des Tumeurs Data

To demonstrate that the MPS is also applicable to the whole population of primary breast cancer patients, e.g., basal, HER2-amplified breast cancers, it was applied to a diverse set of patients samples (n=537, ER +/−, HER +/−, PGR +/−, different grade, etc., mean follow-up 65±(SD) 40 months) from the E-MTAB-365 dataset publically available via ArrayExpress. This resulted in a good separation of survival in high risk and intermediate risk versus low risk patients (both p<0.01), as can be seen in FIG. 3 (please note that FIG. 3.A shows a clipping of FIG. 3.B, zoomed in on the time axis), and a HR of 2.72 (1.25-5.92, p<0.01).

(iv) Koo Foundation Sun-Yat-Sen Cancer Center Data

The MPS was tested on another patient cohort consisting of a diverse group of breast cancer patients (n=327, GSE20685, ER+/−, HER+/−, PGR+/−, node negative/positive etc.). This resulted in a HR of 3.53 (1.34-9.30, p<0.01) and a good separation of the low, intermediate and high risk patient groups, see FIG. 4 (please note that FIG. 4.A shows a clipping of FIG. 4.B, zoomed in on the time axis).

(v) Institut Paoli-Calmattes Data

Next the MPS recurrence estimator was applied to a set of 266 early breast cancer patients who underwent surgery at the Institut Paoli-Calmattes. The patients cover a diverse set of breast cancers, ER+/−, HER+/−, PGR+/−, node negative/positive, grades 1/2/3, KI67+/−, and P53+/−. The microarrays of these samples are publically available in the GSE21653 dataset. The HR of the MPS was significant at 2.8 (1.20-6.51, p<0.01), besides the risk stratification of the low risk and high risk Kaplan-Meier survival curves was significant as well (p=0.017), see FIG. 5 (please note that FIG. 5.A shows a clipping of FIG. 5.B, zoomed in on the time axis).

Example 3: Assay Development

Instead of applying, e.g., the mentioned Bayesian or (pseudo-)linear models, on mRNA input data coming from microarrays or RNA sequencing, it may be beneficial in clinical applications to develop dedicated assays to perform the sample measurements, for instance on an integrated platform using qPCR to determine mRNA levels of target genes that are part of the MPS. The RNA/DNA sequences of the disclosed target genes can then be used to determine which primers and probes to select on such a platform.

Validation of such a dedicated MPS assay can be done by using the microarray-based Bayesian or (pseudo-)linear models as a reference model, and verifying whether the developed assay gives similar results on a set of validation samples. Next to a dedicated assay, this can also be done to build and calibrate similar Bayesian or (pseudo-) linear models using mRNA-sequencing data as input measurements.

Example 4: CDS Application

With reference to FIG. 6 (diagrammatically showing a clinical decision support (CDS) system configured to determine a risk score that indicates a risk that a clinical event will occur within a certain period of time, as disclosed herein), a clinical decision support (CDS) system 10 is implemented as a suitably configured computer 12. The computer 12 may be configured to operate as the CDS system 10 by executing suitable software, firmware, or other instructions stored on a non-transitory storage medium (not shown), such as a hard drive or other magnetic storage medium, an optical disk or another optical storage medium, a random access memory (RAM), a read-only memory (ROM), a flash memory, or another electronic storage medium, a network server, or so forth. While the illustrative CDS system 10 is embodied by the illustrative computer 12, more generally the CDS system may be embodied by a digital processing device or an apparatus comprising a digital processor configured to perform clinical decision support methods as set forth herein. For example, the digital processing device may be a handheld device (e.g., a personal data assistant or smartphone running a CDS application), a notebook computer, a desktop computer, a tablet computer or device, a remote network server, or so forth. The computer 12 or other digital processing device typically includes or is operatively connected with a display device 14 via which information including clinical decision support recommendations are displayed to medical personnel. The computer 12 or other digital processing device typically also includes or is operatively connected with one or more user input devices, such as an illustrative keyboard 16, or a mouse, a trackball, a trackpad, a touch sensitive screen (possibly integrated with the display device 14), or another pointer based user input device, via which medical personnel can input information such as operational commands for controlling the CDS system 10, data for use by the CDS system 10, or so forth.

The CDS system 10 receives as input information pertaining to a subject (e.g., a hospital patient, or an outpatient being treated by an oncologist, physician, or other medical personnel, or a person undergoing cancer screening or some other medical diagnosis who is known or suspected to have a certain type of cancer such as colon cancer, breast cancer, or liver cancer, or so forth). The CDS system 10 applies various data analysis algorithms to this input information in order to generate clinical decision support recommendations that are presented to medical personnel via the display device 14 (or via a voice synthesizer or other device providing human-perceptible output). In some embodiments, these algorithms may include applying a clinical guideline to the patient. A clinical guideline is a stored set of standard or "canonical" treatment recommendations, typically constructed based on recommendations of a panel of medical experts and optionally formatted in the form of a clinical "flowchart" to facilitate navigating through the clinical guideline. In various embodiments the data processing algorithms of the CDS 10 may additionally or alternatively include various diagnostic or clinical test algorithms that are performed on input information to extract clinical decision recommendations, such as machine learning methods disclosed herein.

In the illustrative CDS systems disclosed herein (e.g., CDS system 10), the CDS data analysis algorithms include one or more diagnostic or clinical test algorithms that are performed on input genomic and/or proteomic information acquired by one or more medical laboratories 18. These laboratories may be variously located "on-site", that is, at the hospital or other location where the subject is undergoing medical examination and/or treatment, or "off-site". e.g., a specialized and centralized laboratory that receives (via mail or another delivery service) a sample of a tissue and/or cells and/or a body fluid of the subject that has been extracted from the subject (e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, preferably via a biopsy procedure or other sample extraction procedure). The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, the body fluid of which a sample is extracted may be urine, gastrointestinal contents, or an extravasate.

The extracted sample is processed by the laboratory to generate genomic or proteomic information. For example, the extracted sample may be processed using a microarray (also variously referred to in the art as a gene chip, DNA chip, biochip, or so forth) or by quantitative polymerase chain reaction (qPCR) processing to measure probative genomic or proteomic information such as expression levels of genes of interest, for example in the form of a level of messenger ribonucleic acid (mRNA) that is transcribed from the gene, or a level of a protein that is translated from the mRNA transcribed from the gene. As another example, the extracted sample may be processed by a gene sequencing laboratory to generate sequences for deoxyribonucleic acid (DNA), or to generate an RNA sequence, copy number variation, methylation, or so forth. Other contemplated measurement approaches include immunohistochemistry (IHC), cytology, fluorescence in situ hybridization (FISH), proximity ligation assay or so forth, performed on a pathology slide. Other information that can be generated by microarray processing, mass spectrometry, gene sequencing, or other laboratory techniques includes methylation information. Various combinations of such genomic and/or proteomic measurements may also be performed.

In some embodiments, the medical laboratories 18 perform a number of standardized data acquisitions on the extracted sample of the tissue and/or the cells and/or the body fluid of the subject, so as to generate a large quantity of genomic and/or proteomic data. For example, the standardized data acquisition techniques may generate an (optionally aligned) DNA sequence for one or more chromosomes or chromosome portions, or for the entire genome of the tissue and/or the cells and/or the body fluid. Applying a standard microarray can generate thousands or tens of thousands of data items such as expression levels for a large number of genes, various methylation data, and so forth. Similarly. PCR-based measurements can be used to measure the expression level of a selection of genes. This plethora of genomic and/or proteomic data, or selected portions thereof, are input to the CDS system 10 to be processed so as to develop clinically useful information for formulating clinical decision support recommendations.

The disclosed CDS systems and related methods relate to processing of genomic and/or proteomic data to assess activity of various cellular signaling pathways and to determine a risk score that indicates a risk that a clinical event (e.g., cancer) occurs within a certain period of time therefrom. However, it is to be understood that the disclosed CDS systems (e.g., CDS system 10) may optionally further include diverse additional capabilities, such as generating clinical decision support recommendations in accordance with stored clinical guidelines based on various patient data such as vital sign monitoring data, patient history data, patient demographic data (e.g., gender, age, or so forth), patient medical imaging data, or so forth. Alternatively, in some embodiments the capabilities of the CDS system 10 may be limited to only performing genomic and/or proteomic data analyses to assess the activity of cellular signaling pathways and to determine a risk score that indicates a risk that a clinical event (e.g., cancer) will occur within a certain period of time therefrom, as disclosed herein.

With continuing reference to exemplary FIG. 6, the CDS system 10 infers activity 22 of two or more cellular signaling pathways, here, the Wnt pathway, the ER pathway, and the HH pathway, in the tissue and/or the cells and/or the body fluid of the subject based at least on, but not restricted to, the expression levels 20 of one or more target gene(s) of the cellular signaling pathways measured in the extracted sample of the tissue and/or the cells and/or body fluid of the subject. Examples disclosed herein relate to the Wnt, ER, AR and HH pathways as illustrative cellular signaling pathways. These pathways are of interest in various areas of oncology because loss of regulation of the pathways can be a cause of proliferation of a cancer. There are about 10-15 relevant signaling pathways, and each cancer is driven by at least one dominant pathway being deregulated. Without being limited to any particular theory of operation these pathways regulate cell proliferation, and consequentially a loss of regulation of these pathways in cancer cells can lead to the pathway being "always on" thus accelerating the proliferation of cancer cells, which in turn manifests as a growth, invasion or metastasis (spread) of the cancer.

Measurement of mRNA expression levels of genes that encode for regulatory proteins of the cellular signaling pathway, such as an intermediate protein that is part of a protein cascade forming the cellular signaling pathway, is an indirect measure of the regulatory protein expression level and may or may not correlate strongly with the actual regulatory protein expression level (much less with the overall activity of the cellular signaling pathway). The cellular signaling pathway directly regulates the transcription of the target genes—hence, the expression levels of mRNA transcribed from the target genes is a direct result of this regulatory activity. Hence, the CDS system 10 infers activity of the two or more cellular signaling pathways (here, the Wnt pathway, the ER pathway, and the HH pathway) based at least on expression levels of one or more target gene(s) (mRNA or protein level as a surrogate measurement) of the cellular signaling pathways. This ensures that the CDS system 10 infers the activity of the pathway based on direct information provided by the measured expression levels of the target gene(s).

The inferred activities, in this example, $P_{Wnt}$, $P_{ER}$, and $P_{HH}$, i.e., the inferred activities of the Wnt pathway, the ER pathway, and the HH pathway, are then used to determine 24 a risk score that indicates a risk that a clinical event, in this example, cancer, in particular, breast cancer, will occur within a certain period of time, as described in detail herein. The risk score is based at least in part on a combination of the inferred activities. For example, the risk score may be the "Multi-Pathway Score" (MPS) calculated as described in detail with reference to equation (7).

Based on the determined MPS, the CDS system 10, in this example, assigns 26 the subject to at least one of a plurality of risk groups associated with different indicated risks that the clinical event will occur within the certain period of time, and/or decides 28 a treatment recommended for the subject based at least in part on the indicated risk that the clinical event will occur within the certain period of time.

Determining the MPS and/or the risk classification for a particular patient by the CDS system or a standalone implementation of the MS and risk classification as described herein will enable the oncologist, physician, or other medical personnel involved in diagnosis or treatment or monitoring/follow-up of the patient to tailor the treatment such that the patient has the best chance of long term survival while unwanted side-effects, especially those of aggressive chemotherapy and/or targeted therapy and/or immunotherapy and/or radiotherapy and/or surgery, are minimized. Thus, e.g., patients with a low risk of cancer recurrence, i.e., those with a low MPS and/or those classified as low risk based on the risk stratification algorithm as described herein, are currently typically treated with hormonal treatment alone or a combination of hormonal treatment, for example anti-estrogen and/or aromatase inhibitors, and a less toxic chemotherapeutic agent. On the other hand, patients with an intermediate or high risk of cancer recurrence, i.e., those with a medium to high MPS and/or those classified as intermediate or high risk based on the risk stratification algorithm as described herein, will currently typically be treated with more aggressive chemotherapy, such as anthracycline and/or taxane-based treatment regimes. In addition, the MPS, possibly in combination with other patient's test results such as $P_{ER}$, $P_{Wnt}$, $P_{HH}$, $P_{AR}$, and/or other prognostic or predictive (e.g., companion diagnostic) test, can give rise to a decision to treat the patient with targeted drugs such as Tamoxifen, Trastuzumab, Bevacizumab. and/or other therapeutic drugs (for example immunotherapy) that are currently not part of the main line treatment protocol for the patient's particular cancer, and/or other treatment options, such as radiation therapy, for example brachytherapy, and/or different timings for treatment, for example before and/or after primary treatment.

It is noted that instead of directly using the determined risk score (MPS) as an indication of the risk that the clinical event (e.g., cancer) will occur within the certain period of time, it is possible that the CDS system 10 is configured to combine the risk score and/or at least one of the inferred activities with one or more additional risk scores obtained from one or more additional prognostic tests to obtain a combined risk score, wherein the combined risk score indicates a risk that the clinical event will occur within the certain period of time. The one or more additional prognostic tests may comprise, in particular, the Oncotype DX® breast cancer test, the Mammostrat® breast cancer test, the MammaPrint® breast cancer test, the BluePrint™ breast cancer test, the CompanDx® breast cancer test, the Breast Cancer Index$^{SM}$ (HOXB13/IL17BR), the OncotypeDX® colon cancer test, and/or a proliferation test performed by measuring expression of gene/protein Ki67.

Example 5: A Kit and Analysis Tools to Determine a Risk Score

The set of target genes which are found to best indicate specific pathway activity, based on microarray/RNA sequencing based investigation using, e.g., the Bayesian model or the (pseudo-)linear model, can be translated into for example a multiplex quantitative PCR assay or dedicated microarray biochips to be performed on a tissue, a cell or a body fluid sample. A selection of the gene sequence as described herein can be used to select for example a primer-probe set for RT-PCR or oligonucleotides for microarray development. To develop such an FDA-approved test for pathway activity and risk score determination, development of a standardized test kit is required, which needs to be clinically validated in clinical trials to obtain regulatory approval.

Example 6: Comparison of Risk Scores

FIG. 7 shows a plot illustrating results from experiments comparing two differently determined risk scores. In particular, a first risk score (MPS) was calculated according to equation (8) and a second risk score was calculated according to equation (7). The first risk score was optimized for breast cancer samples by assigning the logarithm of the hazard ratios determined on the breast cancer samples (GSE6532 and GSE9195), which resulted in $\alpha=\log(1/0.36)$, $\beta=\log(3.67)$ and $\gamma=\log(2.29)$. The values for $\alpha$ and $\beta$ of the second risk score were exemplarily chosen to be equal to 1. The experiment was performed on the GSE21653, GSE20685, and E-TABM-365 datasets and determined the fraction of patients that suffer a recurrence at 10 years after inclusion (sample taking) as a function of the respective risk score (wherein the risk scores are scaled so that they can easily be compared). In total 1130 patients were enrolled of which 1005 had complete survival data. The dashed curve illustrates the results for the first risk score calculated according to equation (8), whereas the solid curve illustrates the results for the second risk score calculated according to equation (7).

What will be acknowledged from the plot is that the second risk score calculated according to equation (7) (solid curve) results in a monotonically increasing risk, whereas the first risk score calculated according to equation (8) (dashed curve) levels off at higher risk scores (it even appears to go down a bit). This means that at the upper end of the first risk score calculated according to equation (8), it is not possible to distinguish the patients' risk anymore, whereas with the second risk score calculated according to equation (7), the risk continuously increases with the risk score.

In addition, it is also clear from the plot that the second risk score calculated according to equation (7) (solid curve) is better able to discriminate high risk patients (0.84 vs. 0.78), but also minutely better at identifying low risk patients (0.43 vs. 0.45) than the first risk score calculated according to equation (8) (dashed curve).

In general, it is to be understood that while examples pertaining to the Wnt pathway, the ER pathway, the AR pathway, and/or the HH pathway are provided as illustrative examples, the approaches for cellular signaling pathway analysis disclosed herein are readily applied to other cellular signaling pathways besides these pathways, such as to intercellular signaling pathways with receptors in the cell membrane and intracellular signaling pathways with receptors inside the cell. In addition: This application describes several preferred embodiments. Modifications and alterations may occur to others upon reading and understanding the preceding detailed description. It is intended that the application be construed as including all such modifications and alterations insofar as they come within the scope of the appended claims or the equivalents thereof.

Other variations to the disclosed embodiments can be understood and effected by those skilled in the art in practicing the claims, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the determination of the risk score performed by one or several units or devices can be performed by any other number of units or devices.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present application mainly relates to specific method for determining a risk score that indicates a risk that a clinical event will occur within a certain period of time, wherein the risk score is based at least in part on a combination of inferred activities of two or more cellular signaling pathways in a tissue and/or cells and/or a body fluid of a subject. The present application also relates to an apparatus comprising a digital processor configured to perform such methods, to a nontransitory storage medium storing instructions that are executable by a digital processing device to perform such methods, and to a computer program comprising program code means for causing a digital processing device to perform such methods.

LITERATURE de Sousa E Melo F, C. S. (2011). Methylation of cancer-stem-cell-associated Wnt target genes predicts poor prognosis in colorectal cancer patients. Cell Stem Cell., 476-485

Hatzis P, v. d. (2008). Genome-wide pattern of TCF7L2/TCF4 chromatin occupancy in colorectal cancer cells. Mol Cell Biol., 2732-2744

Nusse, R. (2012, May 1). Wnt target genes. Retrieved from The Wnt homepage: stanford.edu/group/nusselab/cgi-bin/wnt/target_genes Söderberg O, G. M. (2006). Direct observation of individual endogenous protein complexes in situ by proximity ligation. Nat Methods., 995-1000 van de Wetering M, S. E.-P.-F. (2002). The beta-catenin/TCF-4 complex imposes a crypt progenitor phenotype on colorectal cancer cells. Cell, 241-250

The invention claimed is:

1. A method comprising:
obtaining a sample from a subject, comprising tissue and/or cells and/or a body fluid of the subject;
measuring, from the obtained sample, expression levels of one or more target gene(s) of each of at least three cellular signaling pathways;
inferring, by a processor, activities of the at least three cellular signaling pathways in the tissue and/or cells and/or a body fluid of the subject based at least on the measured expression levels of the one or more target gene(s) of each of the at least three cellular signaling pathways,
determining, by the processor, a risk score that indicates a risk that a clinical event will occur within a certain period of time, based at least in part on a combination of the inferred activities, wherein the clinical event is the occurrence or recurrence of cancer in the subject,
deciding, by the processor, a treatment recommended for the subject based at least in part on the indicated risk that the clinical event will occur within the certain period of time, wherein the recommended treatment comprises at least one or more of hormone treatment and chemotherapy configured to prevent or minimize the occurrence or recurrence of cancer in the subject when the indicated risk is a low risk that the clinical event will occur within the certain period of time, and wherein the recommended treatment comprises at least one or more of chemotherapy, radiation therapy, and immunotherapy configured to prevent or minimize the occurrence or recurrence of cancer in the subject when the indicated risk is an intermediate or high risk that the clinical event will occur within the certain period of time, and
administering the recommended treatment to the subject;
wherein the at least three cellular signaling pathways comprise a Wnt pathway, an ER pathway, and an HH pathway,
wherein the risk score is defined such that the indicated risk that the clinical event will occur within the certain period of time decreases with an increasing $P_{ER}$ and increases with an increasing max $(P_{wnt}, P_{HH})$, and
wherein $P_{ER}$, $P_{wnt}$, and $P_{HH}$ denote the inferred activities of the ER pathway, the Wnt pathway, and the HH pathway, respectively.

2. The method of claim 1, wherein the combination of the inferred activities comprises the expression $$-\alpha \cdot P_{ER} + \beta \cdot \max(P_{wnt}, P_{HH}),$$

wherein $\alpha$ and $\beta$ are positive constant scaling factors, and the indicated risk that the clinical event will take place within the certain period of time monotonically increases with an increasing value of the expression.

3. The method of claim 2, wherein the inferring of the activities of the at least three cellular signaling pathways comprises:
inferring activity of the Wnt pathway in the tissue and/or the cells and/or the body fluid of the subject based at least on expression levels of one or more target gene(s) of the Wnt pathway measured in the extracted sample of the tissue and/or the cells and/or the body fluid of the subject selected from the group consisting of: KIAA1199, AXIN2, RNF43, TBX3, TDGF1, SOX9, ASCL2, IL8, SP5, ZNRF3, KLF6, CCND1, DEFA6, and FZD7, and inferring activity of the ER pathway in the tissue and/or the cells and/or the body fluid of the subject based at least on expression levels of one or more target gene(s) of the ER pathway measured in the extracted sample of the tissue and/or the cells and/or the body fluid of the subject selected from the group consisting of: GREB1, PGR, XBP1, CA12, SOD1, CTSD, IGFBP4, TFF1, SGK3, NRIP1, CELSR2, WISP2, and AP1B1, and inferring activity of the HH pathway in the tissue and/or the cells and/or the body fluid of the subject based at least on expression levels of one or more target gene(s) of the HH pathway measured in the extracted sample of the tissue and/or the cells and/or the body fluid of the subject selected from the group consisting of: GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN, and CTSL1, and inferring activity of an AR pathway in the tissue and/or the cells and/or the body fluid of the subject based at least on expression levels of one or more target gene(s) of the AR pathway measured in the extracted sample of the tissue and/or the cells and/or the body fluid of the subject selected from the group consisting of: KLK2, PMEPA1, TMPRSS2, NKX3 1, ABCC4, KLK3, FKBPS, ELL2, UGT2B15, DHCR24, PPAP2A, NDRG1, LRIG1, CREB3L4, LCP1, GUCY1A3, AR, and EAF2.

4. The method of claim 3, wherein the inferring of the activities of the at least three cellular signaling pathways is further based on:

expression levels of at least one target gene of the Wnt pathway measured in the extracted sample of the tissue and/or the cells and/or the body fluid of the subject selected from the group consisting of: NKD1, OAT, FAT1, LEF1, GLUL, REG1B, TCF7L2, COL18A1, BIVIP7, SLC1A2, ADRA2C, PPARG, DKK1, HNF1A, and LECT2, and/or expression levels of at least one target gene of the ER pathway measured in the extracted sample of the tissue and/or the cells and/or the body fluid of the subject selected from the group consisting of: RARA, MYC, DSCAM, EBAG9, COX7A2L, ERBB2, PISD, KRT19, HSPB1, TRIM25, PIMA, COL18A1, CDH26, NDUFV3, PRDM15, ATPSJ, and ESR1, and/or expression levels of at least one target gene of the HH pathway measured in the extracted sample of the tissue and/or the cells and/or the body fluid of the subject selected from the group consisting of: BCL2, FOXA2, FOXF1, H19, HHIP, IL1R2, JAG2, JUP, MIF, MYLK, NKX2.2, NKX2.8, PITRM1, and TOM1, and/or expression levels of at least one target gene of the AR pathway measured in the extracted sample of the tissue and/or the cells and/or the body fluid of the subject selected from the group consisting of: APP, NTS, PLAU, CDKN1A, DRG1, FGF8, IGF1, PRKACB, PTPN1, SGK1, and TACC2.

5. The method of claim 1, further comprising:
assigning, by the processor, the subject to at least one of a plurality of risk groups associated with different indicated risks that the clinical event will occur within the certain period of time, the plurality of risk groups comprising at least a first risk group wherein the subject has a low risk that the clinical event will occur within the certain period of time, and at least a second risk group wherein the subject has an intermediate or high risk that the clinical event will occur within the certain period of time.

6. The method of claim 5, comprising:
inferring, by the processor, activity of the Wnt pathway in the tissue and/or the cells and/or the body fluid of the subject based at least on expression levels of two, three or more target genes of a set of target genes of the Wnt pathway measured in the extracted sample of the tissue and/or the cells and/or the body fluid of the subject, and/or inferring, by the processor, activity of the ER pathway in the tissue and/or the cells and/or the body fluid of the subject based at least on expression levels of two, three or more target genes of a set of target genes of the ER pathway measured in the extracted sample of the tissue and/or the cells and/or the body fluid of the subject, and/or inferring, by the processor, activity of the HH pathway in the tissue and/or the cells and/or the body fluid of the subject based at least on expression levels of two, three or more target genes of a set of target genes of the HH pathway measured in the extracted sample of the tissue and/or the cells and/or the body fluid of the subject, and/or inferring, by the processor, activity of an AR pathway in the tissue and/or the cells and/or the body fluid of the subject based at least on expression levels of two, three or more target genes of a set of target genes of the AR pathway measured in the extracted sample of the tissue and/or the cells and/pr the body fluid of the subject.

7. The method of claim 6, wherein
the set of target genes of the Wnt pathway includes at least nine target genes selected from the group consisting of: KIAA1199, AXIN2, RNF43, TBX3, TDGF1, SOX9, ASCL2, IL8, SP5, ZNRF3, KLF6, CCND1, DEFA6, and FZD7, and/or the set of target genes of the ER pathway includes at least nine target genes selected from the group consisting of: GREB1, PGR, XBPI, CA12, SOD1, CTSD, IGFBP4, TFF1, SGK3, NRIP1, CELSR2, WISP2, and AP1B1, and/or the set of target genes of the HH pathway includes at least nine target genes selected from the group consisting of: GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN, and CTSL1, and/or the set of target genes of the AR pathway includes at least nine target genes selected from the group consisting of: KLK2, PMEPA1, TMPRSS2, NKX3_1, ABCC4, KLK3, FKBPS, ELL2, UGT2B15, DHCR24, PPAP2A, NDRG1, LRIG1, CREB3L4, LCP1, GUCY1A3, AR, and EAF2.

8. The method of claim 7, wherein
the set of target genes of the Wnt pathway further includes at least one target gene selected from the group consisting of: NKD1, OAT, FAT1, LEF1, GLUL, REG1B, TCF7L2, COL18A1, BMP7, SLC1A2, ADRA2C, PPARG, DKK1, HNF1A, and LECT2, and/or the set of target genes of the ER pathway further includes at least one target gene selected from the group consisting of: RARA, MYC, DSCAM, EBAG9, COX7A2L, ERBB2, PISD, KRT19, HSPB1, TRIM25, PTMA, COL18A1, CDH26, NDUFV3, PRDIVI15, ATPSJ, and ESR1, and/or the set of target genes of the HH pathway further includes at least one target gene selected from the group consisting of: BCL2, FOXA2, FOXF1, H19, HHIP, IL1R2, JAG2, JUP, MIF, MYLK, NKX2.2, NKX2.8, PITRM1 and TOM1, and/or the set of target genes of the AR pathway further includes at least one target gene selected from the group consisting of: APP, NTS, PLAU, CDKN1A, DRG1, FGF8, IGF1, PRKACB, PTPN1, SGK1, and TACC2.

9. The method of claim 8, further comprising combining, by the processor, the risk score and/or at least one of the inferred activities with one or more additional risk scores obtained from one or more additional prognostic tests to obtain a combined risk score, wherein the combined risk score indicates a risk that the clinical event will occur within the certain period of time.

10. The method of claim 9, further comprising the step of providing, to medical personnel via a display device in communication with the processor, the obtained combined risk score.

11. The method of claim 1, wherein the at least three cellular signaling pathways further comprise an AR pathway.

12. The method of claim 1, further comprising the step of extracting mRNA from the obtained sample, wherein the step of measuring expression levels of one or more target gene(s) of each of the at least three cellular signaling pathways comprises analysis of the extracted mRNA.

13. The method of claim 1, further comprising the step of providing, to medical personnel via a display device in communication with the processor, the determined risk score.

14. The method of claim 1, further comprising the step of providing, to medical personnel via a display device in communication with the processor, the decided treatment recommended for the subject.

15. A method for treating a subject determined to comprise a risk that cancer will occur within a certain period of time, comprising:

receiving a risk score for the subject indicating a risk that cancer will occur within the certain period of time, wherein the risk score is generated by the steps:

(i) receiving measured expression levels of one or more target genes of each of at least three cellular signaling pathways, wherein the expression levels are measured from a sample from a subject, the sample comprising tissue and/or cells and/or a body fluid of the subject;

(ii) inferring activities of the at least three cellular signaling pathways in the tissue and/or cells and/or body fluid of the subject based at least on the expression levels of the one or more target genes of each of the at least three cellular signaling pathways;

(iii) determining a risk score that indicates a risk that cancer will occur within a certain period of time, based at least in part on a combination of the inferred activities, wherein the at least three cellular signaling pathways comprise a Wnt pathway, an ER pathway, and an HH pathway, wherein the risk score is defined such that the indicated risk that the cancer will occur within the certain period of time decreases with an increasing $P_{ER}$ and increases with an increasing max $(P_{wnt}, P_{HH})$, and wherein $P_{ER}$, $P_{wnt}$, and $P_{HH}$ denote the inferred activities of the ER pathway, the Wnt pathway, and the HH pathway, respectively;

identifying a treatment recommended for the subject based at least in part on the received risk for the subject that the cancer will occur within the certain period of time, and administering the identified treatment to the subject, wherein the recommended treatment comprises at least one or more of hormone treatment and chemotherapy configured to prevent or minimize occurrence or recurrence of cancer in the subject when the received risk is a low risk that the clinical event will occur within the certain period of time, and wherein the recommended treatment comprises at least one or more of chemotherapy, radiation therapy, and immunotherapy configured to prevent or minimize occurrence or recurrence of cancer in the subject when the received risk is an intermediate or high risk that the clinical event will occur within the certain period of time.

16. The apparatus of claim 15, wherein the at least three cellular signaling pathways further comprise an AR pathway.

* * * * *